United States Patent [19]
Wang

[11] Patent Number: 6,025,468
[45] Date of Patent: Feb. 15, 2000

[54] ARTIFICIAL T HELPER CELL EPITOPES AS IMMUNE STIMULATORS FOR SYNTHETIC PEPTIDE IMMUNOGENS INCLUDING IMMUNOGENIC LHRH PEPTIDES

[75] Inventor: Chang Yi Wang, Cold Spring Harbor, N.Y.

[73] Assignee: United Biomedical, Inc., Hauppauge, N.Y.

[21] Appl. No.: 09/100,414

[22] Filed: Jun. 20, 1998

[51] Int. Cl.⁷ .......................... A61K 38/00; A61K 38/24; A61K 39/00
[52] U.S. Cl. .......................... 530/324; 530/313; 530/326; 424/198.1
[58] Field of Search ..................... 530/313, 326, 530/324; 424/198.1

[56] References Cited

U.S. PATENT DOCUMENTS

| | | |
|---|---|---|
| 5,023,077 | 6/1991 | Gevas et al. . |
| 5,759,551 | 6/1998 | Ladd et al. . |

FOREIGN PATENT DOCUMENTS

| | | |
|---|---|---|
| 0 427 347 A1 | 5/1991 | European Pat. Off. . |
| WO 89/06974 | 8/1989 | WIPO . |
| WO 94/25060 | 11/1994 | WIPO . |
| WO 95/11998 | 5/1995 | WIPO . |

OTHER PUBLICATIONS

Babbitt et al., (1985) *Nature,* 317:359–361.
Bonneau et al., (1994) *J. Anim. Sci.,* 72:14–20.
Borras–Cuesta et al., (1987) *Eur. J. Immunol.* 17:1213–1215.
Cease et al., (1987) *Proc. Natl. Acad. Sci.* 84:4249–4253.
Cornette et al., (1989) *Methods in Enzymology* 178:611–634.
Ennis et al., (1993) *J. Exp. Med.* 177:207–212.
Ferrari et al., (1991) *J. Clin. Invest.* 88:214–222.
Greenstein et al., (1992) *J. Immunol.* 148 (12):3970–3977.
Meister et al., (1995) *Vaccine* 13 (6):581–591.
Partidos et al., (1991) *J. Gen. Virology* 71:1293–1299.
Rothbard et al., (1988) *EMBO Journal* 7 (1):93–100.
Rudensky et al., (1991) *Nature* 353:622–627.
Sinigaglia et al., (1995) *Immunol. Recogn. of Peptides in Medicine and Biology* chap. 6:79–87.
Schutze et al., (1985) *J. Immunol.* 135 (4):2319–2322.
Stagg et al., (1993) *Immunol.* 79:1–9.

*Primary Examiner*—Christina Y. Chan
*Assistant Examiner*—Ronald Pelley
*Attorney, Agent, or Firm*—Morgan & Finnegan, LLP

[57] ABSTRACT

The present invention is directed to novel peptide immunogens for eliciting antibodies to LHRH comprising artificial T helper cell epitopes (Th epitopes) designed to provide optimum immunogenicity. The artificial Th epitopes are covalently linked to LHRH and optionally an immunostimulatory seqence.

16 Claims, 3 Drawing Sheets

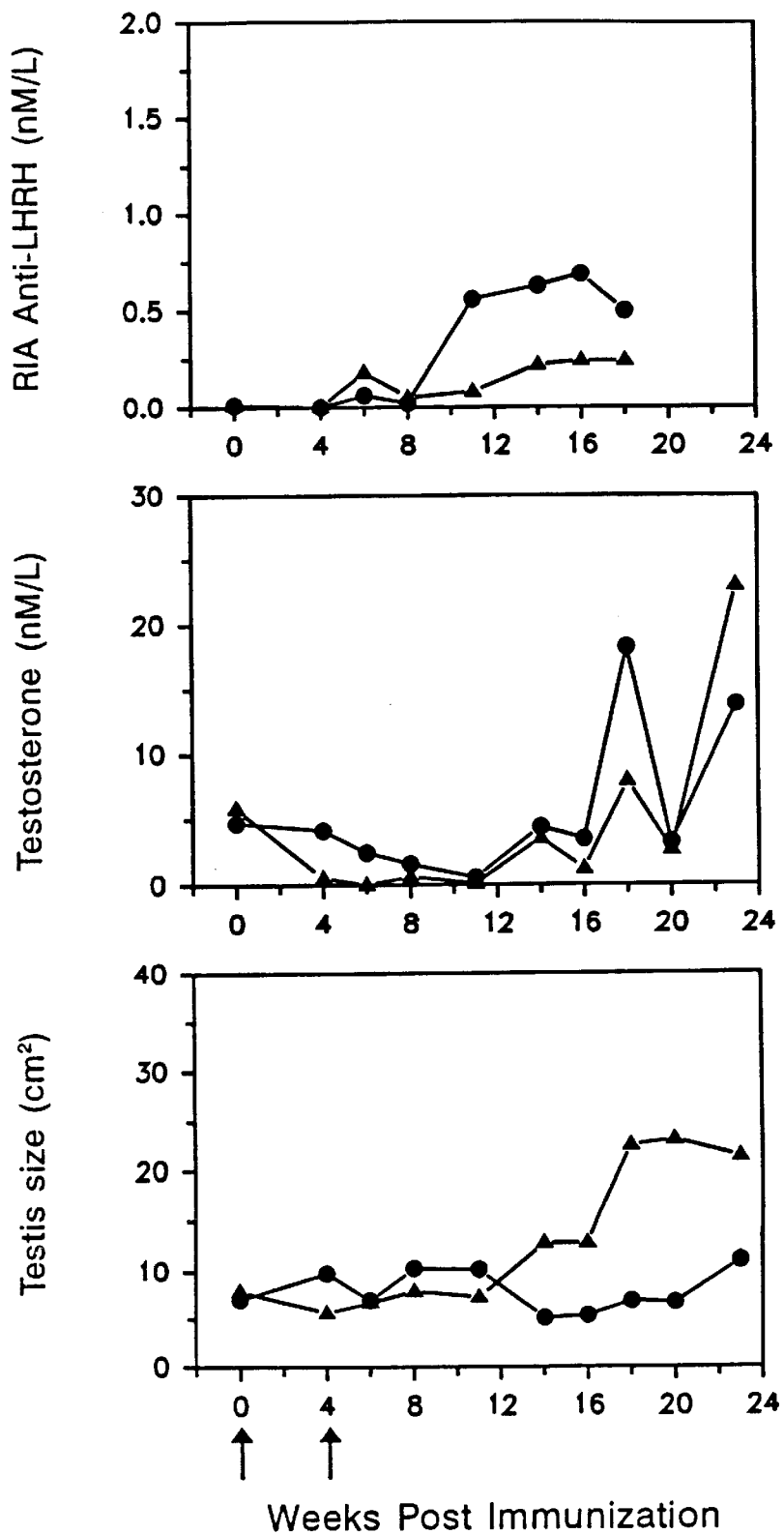
Figure 1. Th/LHRH in Alum

Figure 2. Th/LHRH in IFA
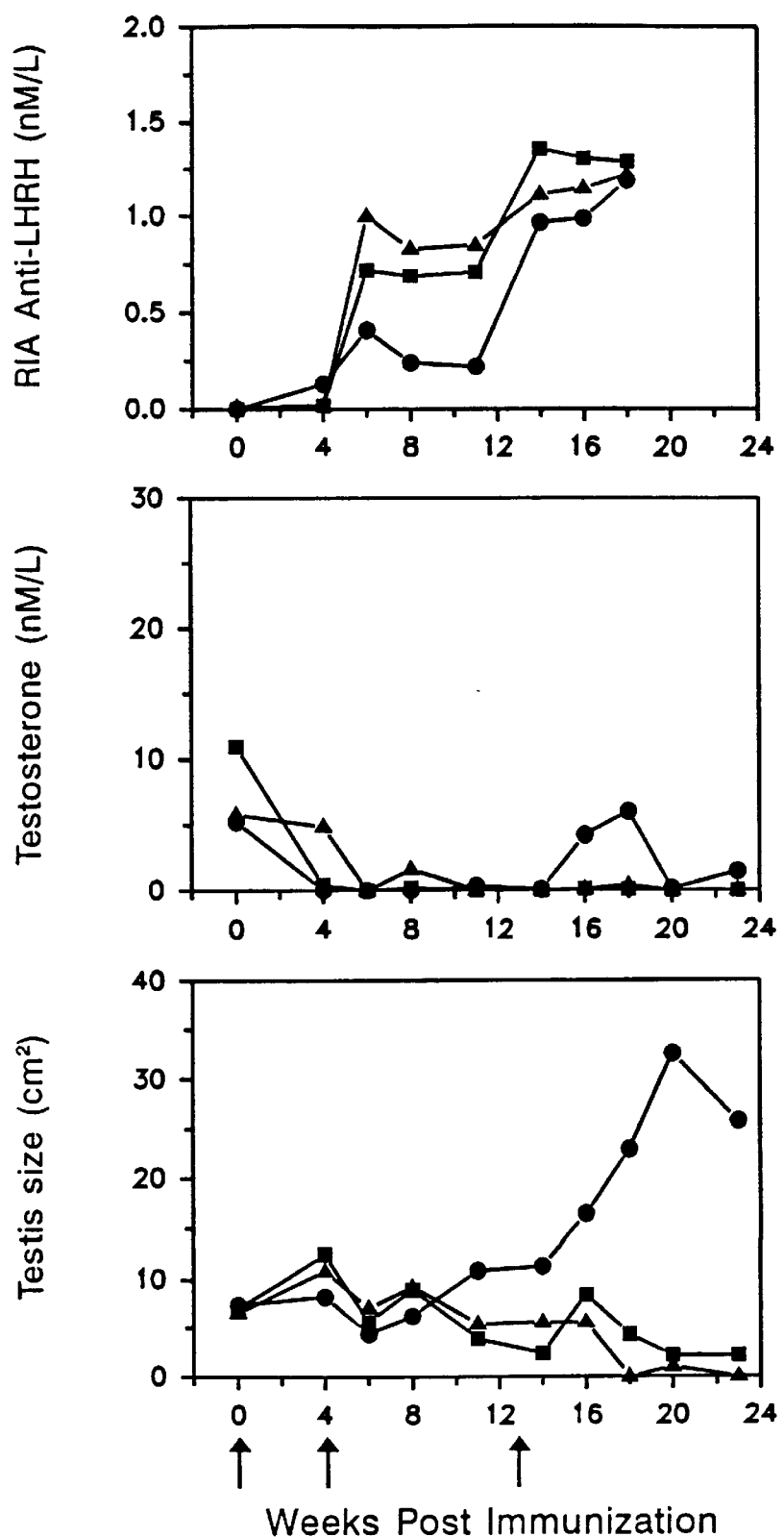
Weeks Post Immunization

Figure 3. Th/LHRH in ISA206/DDA
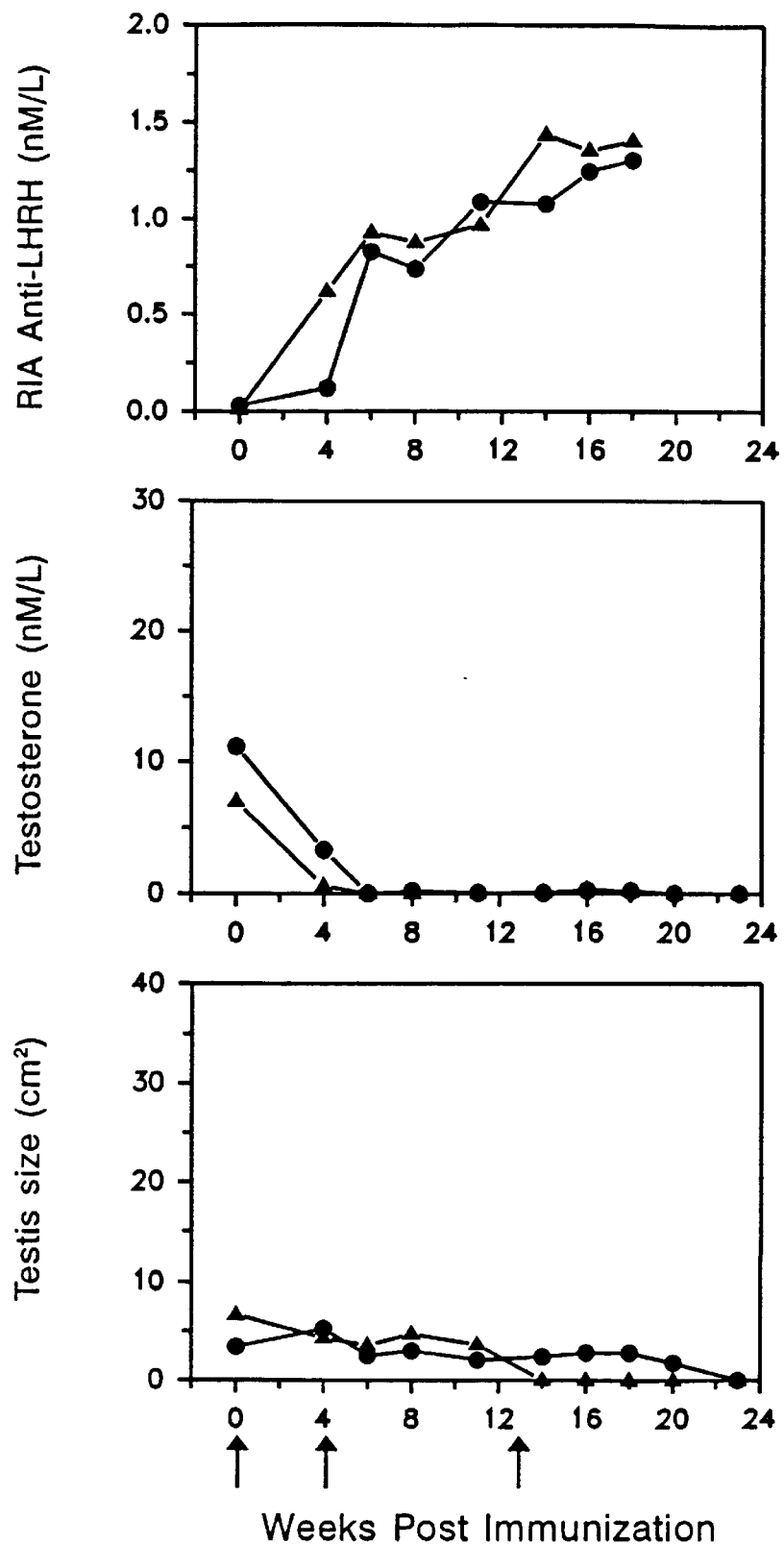

ARTIFICIAL T HELPER CELL EPITOPES AS IMMUNE STIMULATORS FOR SYNTHETIC PEPTIDE IMMUNOGENS INCLUDING IMMUNOGENIC LHRH PEPTIDES

FIELD OF THE INVENTION

This invention relates to a peptide immunogen comprising a novel artificial T helper cell epitope (Th) covalently linked to a desired target antigenic site comprising B cell epitopes and optionally a general immune stimulator sequence. The artificial Th epitope imparts to the peptide immunogen the capability to induce strong T helper cell-mediated immune responses and the production of antibodies directed against the "target antigenic site." The invention also provides for the advantageous replacement of carrier proteins and pathogen-derived T helper cell sites in established peptide immunogens by the novel artificial T helper cell epitopes for improved immunogenicity.

Many rules have been developed for predicting the amino acid sequences of T cell epitopes. However, because there is no central unifying theory on how or what makes a particular amino acid sequence useful as a T cell epitope, the rules are empirical and are not universally applicable. Being aware of these rules, the novel artificial T helper cell epitopes of the present invention were developed, nevertheless, by empirical research.

The peptide immunogens of the present invention are useful for evoking antibody responses in an immunized host to a desired target antigenic site, including sites taken from pathogenic organisms, and sites taken from normally immunosilent self-antigens and tumor-associated targets. Accordingly, the peptides of the invention are useful in diverse medical and veterinary applications, such as: vaccines to provide protective immunity from infectious disease; immunotherapies for treating disorders resulting from malfunctioning normal physiological processes; immunotherapies for treating cancer and as agents to intervene in normal physiological processes to produce desirable results.

For example, the novel artificial T helper cell epitopes of the present invention provide novel short peptide immunogens that elicit antibodies targeted to luteinizing hormone-releasing hormone (LHRH) and are useful for contraception, control of hormone-dependent tumors, prevention of boar taint, and immunocastration. The novel artificial Th epitopes of the present invention have been found to provoke an immune response when combined with target B cell epitopes of various microorganisms/proteins/peptides. In addition to LHRH, the artificial Th epitopes of the present invention have been found to be useful when linked to other target antigenic sites include somatostatin for growth promotion in farm animals; IgE for treatment of allergy; the CD4 receptor of T helper cells for treatment and prevention of HIV infection and immune disorders and foot-and-mouth disease virus capsid protein for prevention of foot-and-mouth disease.

BACKGROUND OF THE INVENTION

It is known that most antibody immune responses are cell-mediated, requiring cooperative interaction between antigen-presenting cells, B cells (antibody-producing cells which also function as antigen-presenting cells), and T helper (Th) cells. Consequently, the elicitation of an effective antibody response requires that the B cells recognize the target antigenic site (B cell epitope) of a subject immunogen and the T helper cells recognize a Th epitope. Generally, the T helper epitope on a subject immunogen is different from its B cell epitope(s) (Babbitt et al., *Nature*, 1985; 317: 359–361). The B cell epitope is a site on the desired target recognized by B cells which in response produce antibodies to the desired target site. It is understood that the natural conformation of the target determines the site to which the antibody directly binds. The T helper cell recognition of proteins is, however, much more complex and less well understood. (Cornette et al., in *Methods in Enzymology*, vol 178, Academic Press, 1989, pp 611–634).

Under present theories, evocation of a Th cell response requires the T helper cell receptor to recognize not the desired target but a complex on the membrane of the antigen-presenting cell formed between a processed peptide fragment of the target protein and an associated class II major histocompatibility complex (MHC). Thus, peptide processing of the target protein and a three-way recognition is required for the T helper cell response. The three part complex is particularly difficult to define since the critical MHC class II contact residues are variably positioned within different MHC binding peptides (Th epitopes) and these peptides are of variable lengths with different amino acid sequences (Rudensky et al., *Nature*, 1991; 353:622–627). Furthermore, the MHC class II molecules themselves are highly diverse depending on the genetic make-up of the host.

The immune responsiveness to a particular Th epitope is thus in part determined by the MHC genes of the host. In fact, it has been shown that certain peptides only bind to the products of particular class II MHC alleles. Thus, it is difficult to identify promiscuous Th epitopes, i.e., those that are reactive across species and across individuals of a single species. It has been found that the reactivity of Th epitopes is different even among individuals of a population.

The multiple and varied factors for each of the component steps of T cell recognition: the appropriate peptide processing by the antigen-processing cell, the presentation of the peptide by a genetically determined class II MHC molecule, and the recognition of the MHC molecule/peptide complex by the receptor on T helper cells have made it difficult to determine the requirements for promiscuous Th epitopes that provide for broad responsiveness (Bianchi et al., EP 0427347; Sinigaglia et al., chapter 6 in *Immunological Recognition of Peptides in Medicine and Biology*, ed., Zegers et al., CRC Press, 1995, pp 79–87).

It is clear that for the induction of antibodies, the immunogen must comprise both the B cell determinant and Th cell determinant(s). Commonly, to increase the immunogenicity of a target, the Th response is provided by coupling the target to a carrier protein. The disadvantages of this technique are many. It is difficult to manufacture well-defined, safe, and effective peptide-carrier protein conjugates for the following reasons:

1. Chemical coupling are random reactions introducing heterogeneity of size and composition, e.g., conjugation with glutataraldehyde (Borras-Cuesta et al., *Eur J Immunol*, 1987; 17: 1213–1215);
2. the carrier protein introduces a potential for undesirable immune responses such as allergic and autoimmune reactions (Bixler et al., WO 89/06974);
3. the large peptide-carrier protein elicits irrelevant immune responses predominantly misdirected to the carrier protein rather than the target site (Cease et al., *Proc Natl Acad Sci USA*, 1987; 84: 4249–4253); and
4. the carrier protein also introduces a potential for epitopic suppression in a host which had previously been immunized with an immunogen comprising the same carrier protein. When a host is subsequently immunized with another immunogen wherein the same carrier protein is coupled to a different hapten, the resultant immune response is enhanced for the carrier protein but inhibited for the hapten (Schutze et al., *J Immunol*, 1985; 135: 2319–2322).

To avoid these risks, it is desirable to replace the carrier proteins. T cell help may be supplied to a target antigen peptide by covalent binding to a well-characterized promiscuous Th determinant. Known promiscuous Th are derived from the potent pathogenic agents such as measles virus F protein (Greenstein et al., *J Immunol*, 1992; 148: 3970–3977) and hepatitis B virus surface antigen (Partidos et al., *J Gen Virol* 1991; 72: 1293–1299). The present inventors have shown that many of the known promiscuous Th are effective in potentiating a poorly immunogenic peptide, such as the decapeptide hormone luteinizing hormone-releasing hormone (LHRH) (U.S. Pat. No. 5,759,551). Other chimeric peptides comprising known promiscuous Th epitopes with poorly immunogenic synthetic peptides to generate potent immunogens have been developed (Borras-Cuesta et al., 1987). Well-designed promiscuous Th/B cell epitope chimeric peptides are capable of eliciting Th responses with resultant antibody responses targeted to the B cell site in most members of a genetically diverse population (U.S. Pat. No. 5,759,551).

A review of the known promiscuous Th epitopes shows that they range in size from approximately 15 to 50 amino acid residues (U.S. Pat. No. 5,759,551) and often share common structural features with specific landmark sequences. For example, a common feature is the presence of amphipathic helices. These are alpha-helical structures with hydrophobic amino acid residues dominating one face of the helix and charged and polar resides dominating the surrounding faces (Cease et al., 1987). Known promiscuous Th epitopes also frequently contain additional primary amino acid patterns such as a charged residue, -Gly-, followed by two to three hydrophobic residues, followed in turn by a charged or polar residue (Rothbard and Taylor, *EMBO J*, 1988; 7:93–101). Th epitopes with this pattern are called Rothbard sequences. It has also been found that promiscuous Th epitopes often obey the 1, 4, 5, 8 rule, where a positively charged residue is followed by hydrophobic residues at the fourth, fifth and eighth positions, consistent with an amphipathic helix having positions 1, 4, 5 and 8 located on the same face. This pattern of hydrophobic and charged and polar amino acids may be repeated within a single Th epitope (Partidos et al., *J Gen Virol*, 1991; 72:1293–99). Most, if not all, of the known promiscuous T cell epitopes contain at least one of the periodicities described above.

Promiscuous Th epitopes derived from pathogens include the hepatitis B surface and core antigen helper T cell epitopes (HBsAg Th and HBc Th), the pertussis toxin helper T cell epitopes (PT Th), the tetanus toxin helper T cell epitopes (TT Th), the measles virus F protein helper T cell epitopes (MVF Th), the *Chlamydia trachomatis* major outer membrane protein helper T cell epitopes (CT Th), the diphtheria toxin helper T cell epitopes (DT Th), the *Plasmodium falciparum* circumsporozoite helper T cell epitopes (PF Th), the *Schistosoma mansoni* triose phosphate isomerase helper T cell epitopes (SM Th), and the Escherichia coli TraT helper T cell epitopes (TraT Th). The sequences of these pathogen-derived Th epitopes can be found in U.S. Pat. No. 5,759,551 as SEQ ID NOS:2–9 and 42–52 therein, incorporated herein by reference; in Stagg et al., *Immunology*, 1993; 79;1–9; and in Ferrari et al., *J Clin Invest*, 1991; 88: 214–222, also incorporated by reference.

The use of such pathogen-derived sites for the immunopotentiation of peptide B cell sites for application to LHRH has been described in U.S. Pat. No. 5,759,551, for HIV in Greenstein et al. (1992), for malaria in EP 0 427,347, for rotavirus in Borras-Cuesta et al. (1987), and for measles in Partidos et al. (1991).

Useful Th epitopes may also include combinatorial Th epitopes. In Wang et al. (WO 95/11998), a particular class of combinatorial Th epitopes, a "Structured Synthetic Antigen Library" (SSAL) was described. Th SSAL epitopes comprise a multitude of Th epitopes with amino acid sequences organized around a structural framework of invariant residues with substitutions at specific positions. The sequences of the SSAL are determined by retaining relatively invariant residues while varying other residues to provide recognition of the diverse MHC restriction elements. This may be accomplished by aligning the primary amino acid sequence of a promiscuous Th, selecting and retaining as the skeletal framework the residues responsible for the unique structure of the Th peptide, and varying the remaining residues in accordance with known MHC restriction elements. Lists of the invariant and variable positions with the preferred amino acids of MHC restriction elements are available to obtain MHC-binding motifs. These may be consulted in designing SSAL Th epitopes (Meister et al., Vaccine, 1995; 13:581–591).

The members of the SSAL may be produced simultaneously in a single solid-phase peptide synthesis in tandem with the targeted B cell epitope and other sequences. The Th epitope library sequences are designed to maintain the structural motifs of a promiscuous Th epitope and at the same time, accommodate reactivity to a wider range of haplotypes. For example, the degenerate Th epitope "SSAL1 TH1" (WO 95/11998), was modeled after a promiscuous epitope taken from the F protein of the measles virus (Partidos et al., 1991). SSAL1 TH1 was designed to be used in tandem with a target antigen, LHRH. Like the measles epitope from which it was derived, SSAL1 TH1 was designed to follow the Rothbard sequence and the 1, 4, 5, 8 rules and is a mixture of four peptides:

```
1                   5                  10
Asp-Leu-Ser-Asp-Leu-Lys-Gly-Leu-Leu-Leu-His-Lys-Leu-Asp-Gly-Leu    (SEQ ID NO:2)
Glu Ile         Glu Ile Arg     Ile Ile Ile     Arg Ile Glu     Ile    (SEQ ID NO:3)
    Val             Val             Val Val Val     Val         Val    (SEQ ID NO:4)
    Phe             Phe             Phe Phe Phe     Phe         Phe    (SEQ ID NO:5)
```

A charged residue Glu or Asp is added at position 1 to increase the charge surrounding the hydrophobic face of the Th. The hydrophobic face of the amphipathic helix is then maintained by hydrophobic residues at 2, 5, 8, 9, 10, 13 and 16. Positions at 2, 5, 8, 9, 10, and 13 are varied to provide a facade with the capability of binding to a wide range of MHC restriction elements. The net effect of the SSAL feature is to enlarge the range of immune responsiveness of the artificial Th (WO 95/11998).

Other attempts have been made to design "idealized" artificial Th epitopes" incorporating all of the properties and features of known promiscuous Th epitopes. Several peptide immunogens comprising these artificial promiscuous Th epitopes, including those in the form of SSAL, have also been constructed. The artificial Th sites have been combined with peptide sequences taken from self-antigens and foreign antigens to provide enhanced antibody responses to site -specific targets (WO 95/11998) that have been described as highly effective. Such peptide immunogens are preferred for providing effective and safe antibody responses, and for their immunopotency, arising from a broadly reactive responsiveness imparted by the idealized promiscuous Th site described.

SUMMARY OF THE INVENTION

The present invention provides an immunogenic peptide composition comprising a promiscuous artificial T helper cell epitope linked to a synthetic peptide B cell epitope or "target antigenic site". The immunogenic peptide comprise an artificial T helper cell (Th) epitopes and a target antigenic site containing B cell epitopes and, optionally, a general immune stimulator sequence. The presence of an artificial Th epitope in the immunogenic peptide impart thereto a capability to induce a strong T helper cell-mediated immune response with the production of a high level of antibodies directed against the "target antigenic site." The present invention further provides for the advantageous replacement of carrier proteins and pathogen-derived T helper cell sites in established peptide immunogens with artificial T helper cell epitopes designed specifically to improve their immunogenicity. The novel short peptide immunogens with the artificial Th epitpoes of the present invention elicit a high level of antibodies targeted to luteinizing hormone-releasing hormone (LHRH) useful for contraception, the control of hormone-dependent tumors, the prevention of boar taint, and immunocastration.

The artificial Th epitopes were developed empirically, mindful of the known rules for predicting promiscuous T cell epitopes. In the absence of a unifying theory explaining the mechanism of Th epitopes, these "predictive" rules serve merely as guidelines for designing effective artificial Th epitopes. The artificial Th epitopes of the present invention have been found to be useful when linked to target antigenic sites and optionally with a immunostimulatory sequence. The immunogenic peptides of the present invention may be represented by the formulae:

$(A)_n$-(Target antigenic site)-$(B)_o$-$(Th)_m$-X or $(A)_n$-$(Th)_m$-$(B)_o$-(Target antigenic site)-X or $(A)_n$-$(B)_o$-$(Th)_m$-$(B)_o$-(Target antigenic site)-X or (Target antigenic site)-$(B)_o$-$(Th)_m$-$(A)_n$-X or $(Th)_m$-$(B)_o$-(Target antigenic site)-$(A)_n$-X wherein: A is an amino acid or a general immunostimulatory sequence, e.g., the invasin domain (Inv) (SEQ ID NO:78) where n is more than one, the individual A's may be the same or different;

B is selected from the group consisting of amino acids, —$NHCH(X)CH_2SCH_2CO$—, —$NHCH(X)CH_2SCH_2CO$($\epsilon$-N)Lys-, —$NHCH(X)CH_2S$-succinimidyl ($\epsilon$-N)Lys-, and —$NHCH(X)CH_2S$-(succinimidyl)-;

Th is an artificial helper T cell epitope selected from the group consisting of SEQ ID NOS:6–22, 31–35 and 105 and an analog or segment thereof;

"Target antigenic site" is a desired B cell epitope, a peptide hapten, or an immunologically reactive analog thereof;

X is an amino acid $\alpha$-COOH or —$CONH_2$;

n is from 1 to about 10;

m is from 1 to about 4; and o is from 0 to about 10.

An example of a peptide hapten as a target antigenic site is LHRH (SEQ ID NO: 77).

The compositions of the present invention comprise peptides capable of evoking antibody responses in an immunized host to a desired target antigenic site. The target antigenic site may be derived from pathogenic organisms and normally immunosilent self-antigens and tumor-associated targets such as LHRH.

Accordingly, the compositions of the present invention are useful in many diverse medical and veterinary applications. These include vaccines to provide protective immunity from infectious disease, immunotherapies for the treatment of disorders resulting from the malfunction of normal physiological processes, immunotherapies for the treatment of cancer, and agents to desirably intervene in and modify normal physiological processes.

In addition to LHRH, other useful targets include: somatostatin for growth promotion in farm animals; IgE for treatment of allergy; the CD4 receptor of T helper cells for treatment and prevention of HIV infection and immune disorders; and foot-and-mouth disease virus capsid protein as a vaccine for the prevention of foot-and-mouth disease.

BRIEF DESCRIPTION OF THE DRAWINGS

In the drawings, the intervals at which the immunogens were administered are shown by arrows at the bottom of each graph. The data for the individual experimental animals in the drawings are represented by solid circles, triangles, and squares.

FIG. 1 graphically depicts anti-LHRH serum antibody levels by RIA, serum testosterone concentrations by RIA, and averaged testes size by cross sectional area, in swine administered the mixture of Th/LHRH peptides (SEQ ID NOS:57, 58, 71 and 75), formulated in alum.

FIG. 2 shows the results for the same mixture formulated in IFA (incomplete Freund's adjuvant).

FIG. 3 shows the results for the same mixture formulated in ISA 206/DDA (dimethyldioctadecylammonium bromide).

DETAILED DESCRIPTION OF THE INVENTION

Idealized artificial Th epitopes have been provided. These are modeled on two known natural Th epitopes and SSAL peptide prototypes, disclosed in WO 95/11998. The SSALS incorporate combinatorial MHC molecule binding motifs (Meister et al., 1995) intended to elicit broad immune responses among the members of a genetically diverse population. The SSAL peptide prototypes were designed based on the Th epitopes of the measles virus and hepatitis B virus antigens, modified by introducing multiple MHC-binding motifs. The design of the other Th epitopes were modeled after other known Th epitopes by simplifying, adding, and/or modifying, multiple MHC-binding motifs to produce a series of novel artificial Th epitopes. The newly adapted promiscuous artificial Th sites were incorporated into synthetic peptide immunogens bearing a variety of target antigenic sites. The resulting chimeric peptides were able to stimulate effective antibody responses to the target antigenic sites.

The prototype artificial helper T cell (Th) epitope shown in Table 1a as "SSAL1 TH1" a mixture of four peptides: SEQ ID NOS:2, 3, 4 and 5 is an idealized Th epitope modeled from a promiscuous Th epitope of the F protein of measles virus (Partidos et al. 1991). The model Th epitope, shown in Table 1a as "MVF Th" (SEQ ID NO:1) corresponds to residues 288–302 of the measles virus F protein. MVF Th (SEQ ID NO:1) was modified to the SSAL1 Th1 prototype (SEQ ID NOS:2, 3, 4 and 5) by adding a charged residue Glu/Asp at position 1 to increase the charge surrounding the hydrophobic face of the epitope; adding or retaining a charged residues or Gly at positions 4, 6, 12 and 14; and adding or retaining a charged residue or Gly at positions 7 and 11 in accordance with the "Rothbard Rule". The hydrophobic face of the Th epitope comprise residues at positions 2, 5, 8, 9, 10, 13 and 16. Hydrophobic residues commonly associated with promiscuous epitopes were substituted at these positions to provide the combinatorial Th SSAL epitopes, SSAL1 Th1 (SEQ ID NOS:2, 3, 4 and 5). The hydrophobic residues conforming to the Rothbard sequence rule are shown in bold (Table 1a, SEQ ID NOS:2, 3, 4 and 5). Positions in the sequence obeying the 1, 4, 5, 8 rule are underlined. Another significant feature of the prototype SSAL1 Th1 (SEQ ID NOS:2, 3, 4 and 5) is that positions 1 and 4 is imperfectly repeated as a palindrome on either side of position 9, to mimic an MHC-binding motif. This "1, 4, 9" palindromic pattern of SSAL1 Th1 was further modified in SEQ ID NOS:6, 7, and 8 (Table 1a) to more closely reflect the sequence of the original MVF model Th (SEQ ID NO:1). Also, the hydrophobicity of the SSAL1 Th1 prototype (SEQ ID NOS:2, 3, 4 and 5) was modulated in SEQ ID NOS:6, 7, and 8 by the addition of methionine residues at variable positions 1, 12, and 14. Experimental data shows that SEQ ID NOS:6, 7, and 8 coupled to a target antigenic site enhanced the antibody response in the immunized animals to the target antigenic site.

SEQ ID NOS:6, 7, and 8 was simplified to SEQ ID NOS:6, 9, 10 and 11 (Table 1a) to provide further immunogenic SSAL Th epitopes. SEQ ID NOS:6, 7, and 8 was further simplified to SEQ ID NOS:12–14 (Table 1a) to provide a series of single-sequence epitopes. SSAL Th SEQ ID NOS:6, 9, 10 and 11 and the single sequence Th epitopes SEQ ID NOS:6, 12–14, coupled to target antigenic sites also provided enhanced immunogenicity It was found that the immunogenicity of SEQ ID NOS:6, 7 and 8 may be improved by extending the N terminus with a non-polar and a polar uncharged amino acid, e.g., Ile and Ser, and extending the C terminus by a charged and hydrophobic amino acid, e.g., Lys and Phe. This is shown in Table 1a as SEQ ID NOS:15, 16 and 17 from which simplified SSAL Th epitopes SEQ ID NOS:15 and 18, and 105 and 19 were derived. Peptide immunogens comprising a target antigenic site and a Th epitope selected from SEQ ID NOS: 15–17, 15 and 18, nd 105 and 19 displayed enhanced immunogenicity. Single-sequence peptides such as SEQ ID NOS:15, 20–22 were also synthesized and tested for immunogenicity in animals. These were also found to be effective Th epitopes.

The SSAL artificial helper epitope shown in Table 1b as "SSAL2 Th2" (SEQ ID NOS:26–30) was modeled after a promiscuous epitope from the hepatitis B virus surface antigen SEQ ID NO: 23 corresponding to residues 19–33 of the hepatitis B surface antigen (HBsAg) (Greenstein et al. 1992). The pathogen-derived model Th, was modified to SEQ ID NO:24 by adding three Lysines to improve solubility in water; the C-terminal Asp was deleted in SEQ ID NO:25 to facilitate the synthesis of chimeric peptides wherein Gly-Gly was introduced as spacers. The SSAL2 Th2 (SEQ ID NOS:26–30) was further modified from SEQ ID NO:24 by varying the positively charged residues therein at positions 1, 2, 3 and 5 to vary the charge surrounding the hydrophobic face of the helical structure. A charged amino acid at variable position 3 also contributed a required residue to generate the idealized Th epitope, SSAL2 Th2 (SEQ ID NOS:26–30), which obeyed the 1, 4, 5, 8 rule (underlined residues). The hydrophobic face of the amphipathic helix consists of hydrophobic residues at positions 4, 6, 7, 10, 11, 13, 15 and 17 of SEQ ID NOS:26–30. The Rothbard sequence residues are shown in bold for prototype SSAL2 Th2 (SEQ ID NOS:26–30).

SEQ ID NOS:31–35 were simplified from the idealized SSAL2 Th2 prototype (SEQ ID NOS:26–30) as described above. For example, variable hydrophobic residues were replaced with single amino acids, such as Ile or Met (SEQ ID NOS:31–35). The hydrophobic Phe in position 4 was incorporated as a feature of SEQ ID NO:34 while deleting the three lysines. The deletion of the C-terminal Asp was incorporated as a feature of SEQ ID NOS:32, 34, and 35. Further modifications included the substitution of the C-termini by a common MHC-binding motif AxTxIL (Meister et al, 1995).

Each of the novel artificial Th epitopes, SEQ ID NOS: 6, 12–19, 105, 20–22 and 31–35 were coupled to a variety of target antigenic sites to provide peptide immunogens. The target antigenic sites include the peptide hormones, LHRH and somatostatin, B cell epitopes from immunoglobulin IgE, the T cell CD4 receptor, and the VP1 capsid protein of foot-and-mouth disease virus. The results show that effective anti-target site antibodies cross-reactive with a diverse group of self-antigens and foreign antigens were produced. Most important, the antibody responses were directed to the target antigenic sites and not to the novel Th epitopes. The results for the novel peptide immunogens for LHRH are shown in Tables 2 and 3. The immunogenicity results also show that the antibodies produced were effective against LHRH but not against the Th epitopes themselves. It is to be emphasized that LHRH is a target antigenic site devoid of T cell epitopes (Sad et al., *Immunology,* 1992; 76: 599–603 and U.S. Pat. No. 5,759,551). Thus, the novel artificial Th epitopes of the present invention represent a new class of promiscuous T helper epitopes.

The artificial Th epitopes of the present invention are contiguous sequences of amino acids (natural or non-natural amino acids) that comprise a class II MHC molecule binding site. They are sufficient to enhance or stimulate an antibody response to the target antigenic site. Since a Th epitope can consist of continuous or discontinuous amino acid segments, not every amino acid of the Th epitope is necessarily involved with MHC recognition. The Th epitopes of the invention further include immunologically functional homologs. Functional Th homologs include immune-enhancing homologs, crossreactive homologs and segments of any of these Th epitopes. Functional Th homologs further include conservative substitutions, additions, deletions and insertions of from one to about 10 amino acid residues and provide the Th-stimulating function of the Th epitope.

The promiscuous Th epitopes of the invention are covalently linked to the N- or C-terminus of the target antigenic site, to produce chimeric Th/B cell site peptide immunogens. The term "peptide immunogen" as used herein refers to molecules which comprise Th epitopes covalently linked to a target antigenic site, whether through conventional peptide bonds so as to form a single larger peptide, or through other forms of covalent linkage, such as a thioester. Accordingly, the Th epitopes (e.g., SEQ ID NOS:6, 12–19, 105, 20–22 and 31–35) are covalently attached to the target antigenic site (e.g., SEQ ID NO:77) either via chemical coupling or via direct synthesis. The Th epitopes may be attached directly to the target site or through a spacer, e.g., Gly-Gly. In addition to physically separating the Th epitope from the B cell epitope (e.g., SEQ ID NOS:41–64, 71–76, 84–90, 92–94, 96–102, 103, 104 and 106), the spacer may disrupt any artifactual secondary structures created by the linking of the Th epitope or its functional homolog with the target antigenic site and thereby eliminate any interference with the Th and/or B cell responses. A flexible hinge spacer that enhances separation of the Th and IgE domains can also be useful. Flexible hinge sequences are often proline rich. One particularly useful flexible hinge is provided by the sequence Pro-Pro-Xaa-Pro-Xaa-Pro (SEQ ID NO:79) modeled from the flexible hinge region found in immunoglobulin heavy chains. Xaa therein is any amino acid, preferably aspartic acid. The conformational separation provided by the spacer (See SEQ ID NOS:80 and 82) permits more efficient interactions between the presented peptide immunogen and the appropriate Th cells arid B cells. Thus the immune responses to the Th epitope is enhanced to provide improved immune reactivity.

The peptide conjugate immunogens of the invention optionally may also comprise a general immunostimulatory peptide sequence. For example, a domain of an invasin protein (Inv) from the bacteria Yersinia spp (Brett et al., *Eur J Immunol,* 1993, 23: 1608–1614). This immune stimulatory property results from the capability of this invasin domain to interact with the β1 integrin molecules present on T cells, particularly activated immune or memory T cells. A preferred embodiment of the invasin domain (Inv) for linkage to a promiscuous Th epitope has been previously described in U.S. Pat. No. 5,759,551 and is incorporated herein by reference. The said Inv domain has the sequence:

Thr-Ala-Lys-Ser-Lys-Lys-Phe-Pro-Ser-Tyr-Thr-Ala-Thr-Tyr-Gln-Phe (SEQ ID NO:78)

or is an immune stimulatory homolog thereof from the corresponding region in another Yersinia species invasin protein. Such homologs thus may contain substitutions, deletions or insertions of amino acid residues to accommodate strain to strain variation, provided that the homologs retain immune stimulatory properties. The general immunostimulatory sequence may optionally be linked to the Th epitope with a spacer sequence.

The peptide conjugates of this invention, i.e., peptide immunogens which comprise the described artificial Th epitopes, can be represented by the formulas:

$(A)_n$-(Target antigenic site)-$(B)_o$-$(Th)_m$-X or $(A)_n$-$(Th)_m$-$(B)_o$-(Target antigenic site)-X or $(A)_n$-$(B)_o$-$(Th)_m$-$(B)_o$-(Target antigenic site)-X -continued or (Target antigenic site)-$(B)_o$-$(Th)_m$-$(A)_n$-X or $(Th)_m$-$(B)_o$-(Target antigenic site)-$(A)_n$-X wherein:

A is optional and is an amino acid or a general immunostimulatory sequence, where n>1, each A may be the same or different;

B is selected from the group consisting of amino acids, —$NHCH(X)CH_2SCH_2CO$—, —$NHCH(X)CH_2SCH_2CO$(ε-N)Lys-, —NHCH (X) $CH_2S$-succinimidyl(ε-N)Lys-, and —$NHCH(X)CH_2S$-(succinimidyl)-;

Th is an artificial helper T cell epitope (SEQ ID NOS: 6, 12–19, 105, 20–22 and 31–35) or an immune enhancing homolog or segment hereof;

"Target antigenic site" is a desired B cell epitope or peptide hapten, or an analog thereof);

X is an amino acid α-COOH or —$CONH_2$;

n is from 1 to about 10;

m is from 1 to about 4; and o is from 0 to about 10.

The peptide immunogens of the present invention comprises from about 25 to about 100 amino acid residues, preferably from about 25 to about 80 amino acid residues.

When A is an amino acid, it can be any non-naturally occurring or any naturally occurring amino acid. Non-naturally occurring amino acids include, but are not limited to, D-amino acids, β-alanine, ornithine, norleucine, norvaline, hydroxyproline, thyroxine, γ-amino butyric acid, homoserine, citrulline and the like. Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. Moreover, when n is greater than one, and two or more of the A groups are amino acids, then each amino acid may be independently the same or different.

When A is an invasin domain sequence, it is preferably an immune stimulatory epitope from the invasin protein of an Yersinia species described here as SEQ ID NO:77.

In one embodiment where n is 3, each A is in turn an invasin sequence (Inv), glycine and glycine.

B is optional and is a spacer comprising one or more naturally occurring or non-naturally occurring amino acids. In $(B)_O$, where O>1, each B may be same or different. B may be Gly-Gly or Pro-Pro-Xaa-Pro-Xaa-Pro (SEQ ID NO:79) or —$NHCH(X)CH_2SCH_2CO$—, —$NHCH(X)CH_2SCH_2CO$(ε-N)Lys-, —$NHCH(X)CH_2S$-succinimidyl(ε-N)Lys-, and —$NHCH(X)CH_2S$-(succinimidyl)-.

Th is a promiscuous T helper cell epitope selected from the group SEQ ID NOS: 6, 12–19, 105, 20–22 and 31–35 and homologs thereof.

The peptide immunogens of this invention, may be made by chemical methods well known to the ordinarily skilled artisan. See, for example, Fields et al., Chapter 3 in *Synthetic Peptides: A User's Guide*, ed. Grant, W. H. Freeman & Co., New York, N.Y., 1992, p.77. The peptides may be synthesized using the automated Merrifield solid phase peptide synthesis with either t-Boc or Fmoc to protect the α-$NH_2$ or side chain amino acids . Equipment for peptide synthesis are available commercially. One example is an Applied Biosystems Peptide Synthesizer Model 430A or 431.

After complete assembly of the desired peptide immunogen, the resin is treated according to standard procedures to cleave the peptide from the resin and de-block the functional groups on the amino acid side chains. The free peptide is purified by HPLC and characterized biochemically, for example, by amino acid analysis, by sequencing, or by mass spectometry. Methods of peptide purification and characterization are well known to one of ordinary skill in the art.

Other chemical means to generate peptide immunogens comprising the Th epitopes of the invention include the ligation of haloacetylated and cysteinylated peptides through the formation of a "thioether" linkage. For example, a cysteine can be added to the C terminus of a Th-containing peptide and the thiol group of cysteine may be used to form a covalent bond to an electrophilic group such as an $N^\alpha$ chloroacetyl-modified or a maleimide-derivatized $\alpha$- or $\epsilon$-$NH_2$ group of a lysine residue, which is in turn attached to the N-terminus of a target antigenic site peptide. In this manner, Th epitope/B cell site conjugates may be obtained.

The subject immunogen may also be polymerized. Polymerization can be accomplished for example by reaction between glutaraldehyde and the —$NH_2$ groups of the lysine residues using routine methodology. By another method, the linear Th/B cell site immunogen can be polymerized or co-polymerized by utilization of an additional cysteine added to the N-terminus of the linear constructs. The thiol group of the N-terminal cysteine can be used for the formation of a "thioether" bond with haloacetyl-modified amino acid or a maleimide-derivatized $\alpha$- or $\epsilon$-$NH_2$ group of a lysine residue that is attached to the N-terminus of a branched poly-lysyl core molecule (e.g., $K_2K$, $K_4K_2K$ or $K_8K_4K_2K$). The subject immunogen may also be polymerized as a branched structure through synthesis of the desired peptide construct directly onto a branched poly-lysyl core resin (Wang, et al., *Science,* 1991; 254:285–288).

The longer synthetic peptide conjugates may alternatively be synthesized by well known nucleic acid cloning techniques. Any standard manual on molecular cloning technology provides detailed protocols to produce peptides comprising the Th epitopes of the invention by expression of recombinant DNA and RNA. To construct a gene expressing a Th/target antigenic site peptide of this invention (e.g., SEQ ID NOS: 6, 12–19, 105, 20–22 and 31–35), the amino acid sequence is reverse translated into a nucleic acid sequence, preferably using optimized codons for the organism in which the gene will be expressed. Next, a gene encoding the peptide is made, typically by synthesizing overlapping oligonucleotides which encode the peptide and necessary regulatory elements. The synthetic gene is assembled and inserted into the desired expression vector. The synthetic nucleic acid sequences encompassed by this invention include those which encode the Th epitopes of the invention and peptides comprising those Th epitopes, the immunologically functional homologs thereof, and nucleic acid constructs characterized by changes in the non-coding sequences that do not alter the immunogenic properties of the peptide or Th epitope encoded thereby. The synthetic gene is inserted into a suitable cloning vector and recombinants are obtained and characterized. The Th epitopes and peptides comprising the Th epitopes are then expressed under conditions appropriate for the selected expression system and host. The Th epitope or peptide is purified and characterized by standard methods.

Peptide immunogens of the invention may be used alone or in combination to elicit antibody responses to Luteinizing Hormone Releasing Hormone. Luteinizing Hormone Releasing Hormone (LHRH) or Gonadotropin-releasing hormone (GnRH) is a master hormone for the regulation of sexual reproduction in both males and females. LHRH regulates the release of LH and FSH which in turn control spermatogenesis, ovulation and estrus, sexual development. LHRH ultimately controls the secretion of the male hormones androgen and testosterone, and the secretion of the female hormones, estrogen and progesterone which themselves are essential for fertility in males and females, respectively. (*Basic and Clinical Endocrinology*, eds. FS Greenspan and JD Baxter, Appleton & Lange:Norwalk Conn. 1994).

Active immunization against LHRH has long been known to exert multiple effects in males including decreased serum and pituitary LH and FSH, reduced serum testosterone, suppression of spermatogenesis and reversible atrophy of the gonads and accessory sex organs. (See, for example, Fraser et al., *J. Endocrinol.,* 1974; 63:399–405; Giri et al., *Exp. Molec. Pathol.,* 1991; 54:255–264; Ladd et al., *J. Reprod. Immunol.,* 1989; 15:85–101; and references cited therein). Immunization against LHRH has been proven useful as a contraceptive in males and has potential as a treatment for prostate cancer (Thau, *Scand J Immunol,* 1992; 36 Suppl 11:127–130; and U.S. Pat. No. 5,759,551).

Immune intervention on the hypothalo-pituitary gonadal axis by active immunization against LHRH can also be used to inhibit sexual hormones in females. Since LHRH regulates the production of FSH by the anterior pituitary which in turn regulates the production of estrogen by the ovaries, blocking the action of LHRH is a therapy for sexual hormone-dependent diseases in women. For example, the ectopic development and maintenance of endometrial tissues outside the uterine musculature is mediated by estrogen. Therefore, blocking the action of LHRH is useful as a treatment for endometriosis. Furthermore, by analogy to prostate cancer, estrogen-driven tumors of the breast should also be responsive to LHRH immunotherapy. Indeed, an anti-LHRH inducing vaccine has been shown to effectively reduce serum levels of LH and FSH in women, an illustration of the potential of this method to effect contraception and treatment of hormone-dependent disorders (Gual et al., *Fertility and Sterility,* 1997; 67: 404–407).

In addition to providing treatment for a number of important diseases and reversible infertility in both men and women, LHRH-based immunotherapy provides a means for reversible contraception in male and female animals (e.g. dogs, cats, horses and rabbits) as well as mitigating undesirable androgen-driven behavior such as heat, territorial marking and aggression.

Lastly, immunological castration (e.g., antibody-based inhibition of LHRH action) has application in the livestock industry. Meat from male animals is not processed into prime cuts because of the presence of an offensive aroma and taste, known as boar taint. Boar taint is conventionally eliminated by mechanical castration; however, castration of male food animals is no longer considered humane. Moreover, mechanical castration results in poorer growth performance and lesions in body part, also referred to as carcass traits, in comparison to non-castrated males. Whereas, the growth performance and carcass traits of immunocastrated animals are less affected than those of castrated animals (Bonneau et al., *J Anim Sci,* 1994; 72: 14–20 and U.S. Pat. No. 5,573,767). Therefore, immunological castration is preferable to mechanical castration.

LHRH (or GnRH) is a self-molecule that must be linked to a Th component in order to generate anti-LHRH antibodies (Sad et al., *Immunology,* 1992; 76: 599–603). Several such immunogenic forms of LHRH have been tested. For example, LHRH immunogens have been produced by conjugation to carrier proteins or linked by peptide synthesis to potent Th sites derived from pathogenic organisms (WO 94/07530, U.S. Pat. No. 5,759,551, Sad et al., 1992). Improved LHRH peptide immunogens comprising LHRH and artificial Th epitopes are exemplified in EXAMPLES 1–3.

This invention also provides for compositions comprising pharmaceutically acceptable delivery systems for the administration of the peptide immunogens. The compositions comprise an immunologically effective amount of one or more of the peptide immunogens of this invention. When so formulated, the compositions of the present invention comprising LHRH or a homolog thereof as target antigenic site, are used for treatment of prostate cancer, prevention of boar taint, immunocastration of animals, the treatment of endometriosis, breast cancer and other gynecological cancers affected by the gonadal steroid hormones, and for contraception in males and females.

The peptide immunogens of the invention can be formulated as immunogenic compositions using adjuvants, emulsifiers, pharmaceutically-acceptable carriers or other ingredients routinely provided in vaccine compositions. Adjuvants or emulsifiers that can be used in this invention include alum, incomplete Freund's adjuvant (IFA), liposyn, saponin, squalene, L121, emulsigen, monophosphoryl lipid A (MPL), QS21, and ISA 720, ISA 51, ISA 35 or ISA 206 as well as the other efficacious adjuvants and emulsifiers. Such formulations are readily determined by one of ordinary skill in the art and also include formulations for immediate release and/or for sustained release. The present vaccines can be administered by any convenient route including subcutaneous, oral, intramuscular, intraperitoneal, or other parenteral or enteral route. Similarly the immunogens can be administered in a single dose or multiple doses. Immunization schedules are readily determined by the ordinarily skilled artisan.

The composition of the instant invention contains an effective amount of one or more of the peptide immunogens of the present invention and a pharmaceutically acceptable carrier. Such a composition in a suitable dosage unit form generally contains about 0.5 $\mu$g to about 1 mg of the peptide immunogen per kg body weight. When delivered in multiple doses, it may be conveniently divided into an appropriate amount per dose. For example, the dose, e.g. 0.2–2.5 mg; preferably 1 mg, may be administered by injection, preferably intramuscularly. This may be followed by repeat (booster) doses. Dosage will depend on the age, weight and general health of the subject as is well known in the vaccine and therapeutic arts.

Vaccines comprising mixtures of the subject peptide immunogens, particularly mixtures comprising Th sites derived from both MVF Th, i.e., and HBsAg Th, i.e., SEQ ID NOS: 6, 12–19, 105, 20–22 and 31–35 may provide enhanced immunoefficacy in a broader population and thus provide an improved immune response to LHRH or other target antigenic site.

The immune response to Th/LHRH peptide conjugates or other Th/target antigenic site conjugates can be improved by delivery through entrapment in or on biodegradable microparticles of the type described by O'Hagan et al. (*Vaccine*, 1991; 9:768). The immunogens can be encapsulated with or without an adjuvant, and such microparticles can carry an immune stimulatory adjuvant. The microparticles can also be coadministered with the peptide immunogens to potentiate immune responses As a specific example, the invention provides a method for inducing anti-LHRH antibody by administering pharmaceutical compositions comprising Th/LHRH peptide immunogens to a mammal for a time and under conditions to produce an infertile state in the mammal. As used herein an infertile state is that state which prevents conception. Infertility can be measured by methods known in the art, e.g. evaluation of spermatogenesis or ovulation, as well as by statistical modeling of experimental animal data. Other indicators of infertility in males includes reduction of serum testosterone to castration levels and involution of the testes. The appropriate dose of the composition is about 0.5 $\mu$g to about 1 mg of each peptide per kg body weight. This dosage may conveniently be divided into appropriate amounts per dose when delivered in multiple doses.

Similarly, the LHRH embodiments of this invention relate to a method for treating androgen-dependent carcinoma by administering the subject peptide compositions to the mammal for a time and under conditions to prevent further growth of the carcinoma. The appropriate unit dose is about 0.5 $\mu$g to about 1 mg of each peptide per kg body weight. This is conveniently divided into the appropriate amounts per application when administered in multiple doses.

Further, the LHRH embodiments relate to a method for improving the organoleptic qualities and tenderness of the meat from male domestic animals while maintaining the advantageous growth performance of intact males. The androgenic steroid hormones of intact males are responsible for fast growth but their presence is accompanied by non-androgenic steroids (e.g., 5 $\propto$ androstenone) and skatole (a product of the microbial metabolism of tryptophan) which impart unpleasant taste and aroma to the meat. This condition, known as boar taint in the case of swine, detracts from the quality of the meat. However, by the active immunization of young males with compositions comprising LHRH peptides of the invention, on a schedule that effects immunocastration in the weeks just prior to slaughter, many of the growth advantages of non-castrated males may be retained while providing meat with improved flavor and tenderness.

The efficacy of the peptide composition of the present invention comprising the target antigenic site, LHRH, can be tested by the procedure described in the Examples 1–3.

EXAMPLE 1

IMMUNIZATION OF RATS WITH PEPTIDE IMMUNOGENS CONTAINING LHRH

Peptides listed in Tables 2a and 2b were synthesized and tested as described below.

A. Peptide synthesis. The peptides listed in Tables 2a and 2b were synthesized individually by the Merrifield solid-phase synthesis technique on Applied Biosystems automated peptide synthesizers (Models 430, 431 and 433A) using Fmoc chemistry. Preparation of peptide constructs comprising structured synthetic antigen libraries (SSALs), e.g., the artificial Th site designated SEQ ID NOS:6–8, was accomplished by providing a mixture of the desired amino acids selected for a given position. After complete assembly of the desired peptide or combinatorial peptides, the resin was treated according to standard procedure using trifluoroacetic acid to cleave the peptide from the resin and deblock the protecting groups on the amino acid side chains.

The cleaved, extracted and washed peptides were purified by HPLC and characterized by mass spectrometry and reverse phase HPLC.

Peptides were synthesized to have the LHRH target antigenic peptide (SEQ ID NO:77) in tandem with each of the designed Th epitopes as listed in Tables 2a and 2b. The Th epitopes were those shown in Tables 1a and 1b (SEQ ID NOS:6–22 and 31–35). For purposes of comparison, prior art peptide immunogens comprising model Th sites (SEQ ID NOS:36 and 65), and prototype Th sites (SEQ ID NOS:37–40 and 66–70) and a peptide/carrier protein conjugate, KLH-LHRH (Table 2b) were also produced and tested. The Th/LHRH and Inv/Th/LHRH peptide constructs were synthesized with gly-gly as a spacer between the target antigenic site and the Th epitope, and with or without gly-gly as a spacer between the Th epitope and the Inv immunostimulatory sequence. In addition, SEQ ID NOS:80–82 were synthesized with SEQ ID NO:79 as a spacer between the Th site and the target antigenic site. The results for peptide immunogens SEQ ID NOS: 80 and 82 are not yet available.

B. Protocols for immunization. The LHRH peptide immunogens shown in Tables 2a and 2b were evaluated on groups of 5 to 10 rats as specified by the experimental immunization protocol outlined below and by serological assays for determination of immunogenicity on serum samples:

Animals: Sprague-Dawley rats, male

Group Size: 5–10 rats/group

Immunogen: individual peptide immunogen

Dose: amount in µg as specified, in 0.5 mL

Adjuvants: (1) Freund's Incomplete Adjuvant (IFA); or (2) Alum (Aluminum hydroxide); One adjuvant per immunogen per group Dose Schedule: 0, 3, and 6 weeks or 0, 3 weeks as specified Route: intramuscular Blood was collected and processed into serum, and stored prior to ELISA and radioimunoassay (RIA) for determination of serum testosterone values.

C. Method for determination of immunogenicity. Antibody activities were determined by ELISA (enzyme-linked immunosorbent assays) using 96-well flat bottom microtiter plates which were coated with the LHRH peptide (SEQ ID NO:77) as immunosorbent. Aliquots (100 µL) of the peptide immunogen solution at a concentration of 5 µg/mL were incubated for 1 hour at 37° C. The plates were blocked by another incubation at 37° C. for 1 hour with a 3% gelatin/PBS solution. The blocked plates were then dried and used for the assay. Aliquots (100 µL) of the test immune sera, starting with a 1:100 dilution in a sample dilution buffer and ten-fold serial dilutions thereafter, were added to the peptide coated plates. The plates were incubated for 1 hour at 37° C.

The plates were washed six times with 0.05% TWEEN® in PBS. 100 µL of horseradish peroxidase labeled goat-anti-rat IgG antibody was added at appropriate dilutions in conjugate dilution buffer (Phosphate buffer containing 0.5M NaCl, and normal goat serum). The plates were incubated for 1 hour at 37° C. before being washed as above. Aliquots (100 µL) of o-phenylenediamine substrate solution were then added. The color was allowed to develop for 5–15 minutes before the enzymatic color reaction was stopped by the addition of 50 µL 2N $H_2SO_4$. The $A_{492nm}$ of the contents of each well was read in a plate reader. ELISA titers were calculated based on linear regression analysis of the absorbances, with cutoff $A_{492nm}$ set at 0.5. This cutoff value was rigorous as the values for diluted normal control samples run with each assay were less than 0.15.

D. Determination of immunogen efficacy. Immunogens were evaluated for efficacy by RIA for serum testosterone values. Serum testosterone levels were measured using an RIA kit from Diagnostic Products (Los Angeles, Calif.) according to manufacturer's instructions. The lower detection limit for testosterone ranged from 0.01 to 0.03 nmol/L. Each sample was analyzed in duplicate. Serum samples were scored as being at castration level when the testosterone level was below limits of detection and as "near castration" at <0.1 nmol/L. Results were verified by comparison to testosterone levels in serum from mechanically castrated rats.

E. Results. Results from serum samples collected at weeks 10 or 12 are presented in Tables 2a and 2b. (The peptides of the Tables are ordered by derivation of their Th epitopes, as was done in Tables 1a and 1b.) ELISA data (not shown) demonstrated that immunization by all the listed immunogens resulted in antibody responses in all animals. The efficacy of the anti-peptide antibody responses, consequential to the cross-reactivity to natural LHRH, was established by determining serum testosterone levels. Those results are summarized in the right columns of Tables 2a and 2b as numbers of animals having castration level serum testosterone per total animals in the group.

The results show that the peptides of the invention, whether with a strong adjuvant IFA and administered 3 times at high dose, or with a weak adjuvant Alum and administered twice at low dose were effective in producing immunocastration. The immunogenicity of the Th sites SEQ ID NOS:6, 9 and 15 were improved by the addition of the Inv domain sequence. See comparisons between SEQ ID NOS:41, 44 and 45, 46 and 33 and SEQ ID NOS:53 and 60. Although, the addition of the Inv domain sequence did not always result in improvement in immunogenicity, e.g., compare SEQ ID NOS: 51 and 52, SEQ ID NOS:61 and 62, and, SEQ ID NOS:74 and 75. Two peptides of the invention (SEQ ID NOS:50 and 76) were tested only at low dose with the weak adjuvant Alum and failed to cause immunocastration, but the results with other peptides, e.g., SEQ ID NO:73, indicate that they would have been effective at a higher dose with a strong adjuvant. Many of the LHRH peptide immunogens of the present invention were significantly more effective at inducing immunocastration than the KLH/LHRH peptide carrier protein conjugate or the peptide immunogens having HbsAg Th (SEQ ID NOS:65 and 66–70). See Table 2b.

Also, the peptide immunogens of the present invention were more easily synthesized than the peptide/carrier conjugate protein or the peptide immunogens having the more complex prototype Th epitopes of the prior art (SEQ ID NOS:2–5 or 26–30). Yet, equivalent or improved immunogenicity with fewer and lower doses were obtained with the peptide immunogens comprising the artificial Th epitopes of the present invention.

A serological analysis of the antibody responses of rats that had received the LHRH peptides of the invention demonstrated that the antibody responses to the peptides was specifically directed to the target antigenic site and not to the novel artificial Th sites. This is a distinct advantage of these peptide immunogens over conventional peptide/carrier protein conjugates. Serum samples from rats that had been immunized with the peptide immunogens shown in Table 3, with 25 µg doses on Alum at 0 and 3 weeks, were compared for reactivities to the LHRH target site and to the Th epitope by ELISAs using the LHRH peptide (SEQ ID NO:77) and the appropriate Th epitope (SEQ ID NOS:15, and 31 or 34) as solid-phase substrates in peptide-based ELISAs. Results for these ELISAs are presented in Table 3 which show that despite high titer responsiveness to the LHRH moiety of the Th/LHRH peptide conjugates, reactivities for the artificial Th sites were at background levels.

EXAMPLE 2

LHRH PEPTIDE MIXTURE FOR INDUCTION OF BROADER IMMUNOCASTRATION IN RATS

Establishing the relative efficacies of the various artificial Th epitope/LHRH constructs as shown above in Example 1 permitted selection of the most effective ones for assembly into a peptide mixture of enhanced immunogenicity. A mixture of Th/LHRH peptide immunogens is more efficacious than any individual peptide within the mixture (U.S. Pat. No. 5,795,551). Moreover, a mixture of individual constructs carrying promiscuous Th epitopes derived from MVF Th (SEQ ID NO:1) and HBsAg Th (SEQ ID NOS:23–25) provide broader response in a genetically diverse population than would a peptide composition having Th epitopes derived from only one promiscuous Th epitope. Therefore, a peptide composition comprising a mixture of peptides of the invention derived from MVF Th and HbSAg Th was assembled and the efficacy of the mixture was tested and compared to compositions comprising the individual peptides of the mixture.

Groups of 6 or 8 male rats were immunized with 25 µg doses (total dose) of the peptide compositions indicated in Table 4. The peptides in the mixture were combined in equimolar proportions. The peptides were formulated with 0.4% Alum and administered intramuscularly on weeks 0 and 3. Serum testosterone levels were followed for 22 weeks and the results were scored as number of animals with castration level of testosterone per total number of animals in the group. These results are presented in Table 4. They demonstrated that the low doses of peptide compositions, given with a relatively ineffective adjuvant, achieved castration levels of testosterone by week 5, and that this response was maintained through week 22. Moreover, the peptide mixture performed significantly better than one of the peptide compositions comprising an individual peptide. It can be assumed that the mixture would have shown improved immunogenicity over the other individual peptide composition had the numbers of experimental animals been larger and more representative of a true population.

EXAMPLE 3

LHRH PEPTIDE MIXTURE AND FORMULATIONS FOR THE IMMUNOCASTRATION OF SWINE

A group test animals have been shown to be more broadly responsive to a mixture of peptide immunogens with different Th epitopes than to a composition containing a single peptide immunogen. However, for the prevention of boar taint in swine, it is necessary that the immunopotent LHRH peptide immunogens be sufficiently potent to elicit the desired response in most animals while being acceptable for use in food animals. It is important that there is no immediate effect adverse to the growth rate and that no residue of the peptide immunogen or the adjuvant is left in the meat or cause lesions in the marketable parts of the carcass.

In order to evaluate the useful immunogenicity of a mixture of inventive LHRH peptides, the mixture was administered to swine in three formulations either in 0.4% Alum, IFA, or ISA 206/DDA. ISA 206/DDA is an oil/water emulsion in which Dimethydioctadecylammonium bromide (DDA) is dispersed into MONTANIDE® ISA 206 at 30 mg/ml (MONTANIDE® ISA 206 is an oily metabolizable solution supplied by SEPPIC Inc. of Fairfield, N.J.). The oil suspension is then emulsified at a 1:1 volume ratio into an aqueous peptide solution which has been adjusted for peptide concentration so as to provide the desired dose of peptide in 0.5 mL of the final preparation.

Immunization Protocol

Animals: Yorkshire Hampshire Cross Swine, males, 3–4 weeks of age non-castrated

Group Size: 2–3 animals/group

Immunogen: Equimolar mixture of SEQ ID NOS:57 and 58, 71 and 75

Dose: 400 µg of peptide(s) in 0.5 mL

Adjuvants:
  (1) 0.4% Alum,
  (2) IFA,
  (3) ISA 206/DDA

Schedule: 0, 4, and 13 weeks or 0, 4 weeks

Route: Intramuscular

The efficacy of the peptide immunogen formulations was monitored by assaying the swine serum samples collected throughout the course of the study, the results are graphically presented in FIGS. 1–3. The assays included an RIA for the determination of the presence of antibodies cross-reactive to native LHRH in solution as described below, and an RIA for testosterone as described in EXAMPLE 1. Further, the average testes cross sectional area was determined by palpitation with a caliper.

Antisera for the anti-LHRH RIA were diluted 1:100 in 1% bovine serum albumin (BSA), pH 7.4. An equal volume of diluted sera was added to 100 µL of [$^{125}$I]-LHRH (New England Nuclear Company, Boston, Mass.) diluted in 1% BSA to contain approximately 15,000 cpm for 5.25 pg LHRH. The solution was incubated overnight at room temperature and antibody-bound LHRH was precipitated with 400 µL of 25% polyethylene glycol (MW 8,000) in 0.01 M phosphate-buffered saline (PBS), pH 7.6, and 200 µL of 5 mg/mL bovine gamma globulin in PBS. Anti-LHRH antibody concentrations are expressed as nmol iodinated LHRH bound per liter of serum (Ladd et al., 1988, *Am J Reprod Immunol*, 17:121–127).

Results are depicted graphically in FIGS. 1–3 for the three assays. The intervals at which the immunogens were administered are shown by arrows at the bottom of the graphs. Determinations for the individual experimental animals in each figure are represented by the solid circles, triangles, and squares. The swine responded immunologically to all three formulations, as shown by the presence of anti-LHRH antibody and the concomitant suppression of testosterone.

The alum preparation (FIG. 1) was least effective producing a lower level of antibody responses. One animal of this group did not achieve the castration level of testosterone until week 11 and both animals in this group did not manifest complete involution of the testes. The animals of the alum group did not receive immunizations at week 13, and the effects of the treatment were reversed.

The animals of the IFA group (FIG. 2) displayed higher levels of antibody responses, with two of the three reaching and holding a castration level of testosterone by week 6. However, upon administration of a booster dose at week 13, the lowest responding swine of the three failed to respond and reverted to a normal level of testosterone and to non-involuted testes. The two responsive animals of this group achieved complete involution of the testes by week 23.

Both swine of the ISA 206/DDA group (FIG. 3) provided high and relatively uniform levels of antibody responses. Immunocastration levels of testosterone in this group were achieved by week 9 and stably maintained through week 12. Both animals were responsive to the boost at week 13 and maintained castration levels of testosterone. The testes of both animals were undetectable by week 23.

From the results obtained the ISA 206/DDA formulation is, thus, most preferred for prevention of boar taint. High and uniform effects on the two animals ere achieved with the ISA 206/DDA formulation. Moreover, the formulation is more acceptable in swine in comparison to the IFA formulation which caused lesions, apparently because the IFA formulation is not readily metabolized.

This demonstrates the efficacy of the artificial Th epitopes of the present invention to stimulate effective antibody responses against LHRH.

TABLE 1

Model, Prototype, and Artificial Idealized Th Epitopes

| Th identifier | | Amino Acid Sequence |
|---|---|---|
| a. MVF Th and Th epitopes therefrom | | |
| MVF Th | SEQ ID NO:1 | LSEIKGVIVHRLEGV |
| SSAL1 Th1 | SEQ ID NO:2 | DLSDLKGLLLHKLDGL |
| | SEQ ID NO:3 | EI EIR III RIE I |
| | SEQ ID NO:4 | V V VVV V V |
| | SEQ ID NO:5 | F F FFF F F |
| | SEQ ID NO:6 | ISEIKGVIVHKIEGI |
| | SEQ ID NO:7 | MT RT TRM TM |
| | SEQ ID NO:8 | L L V |
| | SEQ ID NO:6 | ISEIKGVIVHKIEGI |
| | SEQ ID NO:9 | T RT TR T |
| | SEQ ID NO:10 | MSEIKGVIVHKLEGM |
| | SEQ ID NO:11 | LT MRT TRM TV |
| | SEQ ID NO:6 | ISEIKGVIVHKIEGI |
| | SEQ ID NO:12 | ITEIRTVIVTRIETI |
| | SEQ ID NO:13 | MSEMKGVIVHKMEGM |
| | SEQ ID NO:14 | LTEIRTVIVTRLETV |
| | SEQ ID NO:15 | ISISEIKGVIVHKIEGILF |
| | SEQ ID NO:16 | MT RT TRM TM |
| | SEQ ID NO:17 | L L V |
| | SEQ ID NO:15 | ISISEIKGVIVHKIEGILF |
| | SEQ ID NO:18 | T RT TR T |
| | SEQ ID NO:19 | ISLSEIKGVIVHKLEGMLF |
| | SEQ ID NO:105 | MT MRT TRM TV |
| | SEQ ID NO:15 | ISISEIKGVIVHKIEGILF |
| | SEQ ID NO:20 | ISITEIRTVIVTRIETILF |
| | SEQ ID NO:21 | ISMSEMKGVIVHKMEGMLF |
| | SEQ ID NO:22 | ISLTEIRTVIVTRLETVLF |
| b. HBsAg Th, Prototype and Derivatives | | |
| HBsAg.Th | SEQ ID NO:23 | FFLLTRILTIPQSLD |
| | SEQ ID NO:24 | KKKFFLLTRILTIPQSLD |
| | SEQ ID NO:25 | FFLLTRILTIPQSL |
| SSAL2 Th2 | SEQ ID NO:26 | KKKLFLLTKLLTLPQSLD |
| | SEQ ID NO:27 | RRRIKII RII I L IR |
| | SEQ ID NO:28 | VRVV VV V I V |
| | SEQ ID NO:29 | F FF FF F V F |
| | SEQ ID NO:30 | F |
| | SEQ ID NO:31 | KKKIITITRIITIITTID |
| | SEQ ID NO:32 | KKKIITITRIITIITTI |
| | SEQ ID NO:33 | KKKMMTMTRMITMITTID |
| | SEQ ID NO:34 | ITMDTKFLLASTHIL |
| | SEQ ID NO:35 | KKKFITMDTKFLLASTHIL |

TABLE 2

Immunogenicity of LHRH Peptides

| SEQ ID NO: | Description of Antigenic Peptide | Formulations | no. castrated | | no. castrated |
|---|---|---|---|---|---|
| a. MVF Th Derivatives | | | | | |
| 36 | (SEQ ID NO:1)-GG-(LHRH)[a] | 400 μg/dose IFA (0, 3, 6 wpi) | 8/10 | 400 μg/dose Alum (0, 3, 6 wpi) | 5/5 |
| 37 | (SEQ ID NO:2)-GG-(LHRH)[a] | 400 μg/dose IFA (0, 3, 6 wpi) | 9/10 | 400 μg/dose Alum (0, 3, 6, wpi) | 2/5 |
| 38 | (SEQ ID NO:3)-GG-(LHRH)[a] | | | | |
| 39 | (SEQ ID NO:4)-GG-(LHRH)[a] | | | | |
| 40 | (SEQ ID NO:5)-GG-(LHRH)[a] | | | | |
| 41 | (SEQ ID NO:6)-GG-(LHRH)[a] | 400 μg/dose) IFA (0, 3, 6 wpi) | 6/6 | 25 μg/dose Alum (0, 3, 6 wpi) | 3/8 |
| 42 | (SEQ ID NO:7)-GG-(LHRH)[a] | | | | |
| 43 | (SEQ ID NO:8)-GG-(LHRH)[a] | | | | |
| 41 | (SEQ ID NO:6)-GG-(LHRH)[a] | N.D. | | 25 μg/dose Alum (0, 3, 6 wpi) | 1/6 |
| 44 | (SEQ ID NO:9)-GG-(LHRH)[a] | | | | |
| 45 | (Inv)[b]-GG-(SEQ ID NO:6)-GG-(LHRH)[a] | N.D. | | 25 μg/dose Alum (0, 3, 6 wpi) | 5/5 |
| 46 | (Inv)[b]-GG-(SEQ ID NO:9)-GG-(LHRH) | | | | |
| 47 | (SEQ ID NO:10)-GG-(LHRH)[a] | 100 μg/dose IFA (0, 3, 6 wpi) | 4/6 | 25 μg/dose Alum (0,3 wpi) | 1/8 |
| 48 | (SEQ ID NO:11)-GG-(LHRH)[a] | | | | |
| 45 | (Inv)[b]-GG-(SEQ ID NO:6)-GG-(LHRH)[a] | N.D. | | 25 μg/dose Alum (0,3 wpi) | 2/6 |
| 49 | (SEQ ID NO:12)-GG-(LHRH)[a] | N.D. | | 25 μg/dose Alum (0,3 wpi) | 5/6 |
| 50 | (SEQ ID NO:13)-GG-(LHRH)[a] | N.D. | | 25 μg/dose Alum (0, 3 wpi) | 0/6 |

TABLE 2-continued

Immunogenicity of LHRH Peptides

| SEQ ID NO: | Description of Antigenic Peptide | Formulations | no. castrated | | no. castrated |
|---|---|---|---|---|---|
| 51 | (SEQ ID ND:14)-GG-(LHRH)[a] | N.D. | | 25 μg/dose Alum (0, 3 wpi) | 5/6 |
| 52 | (Inv)[b]-GG-(SEQ ID NO:14)-GG-(LHRH)[a] | N.D. | | 25 μg/dose Alum (0, 3 wpi) | 3/6 |
| 53 | (SEQ ID NO:15)-GG-(LHRH)[a] | N.D. | | 25 μg/dose Alum (0, 3 wpi) | 4/8 |
| 54 | (SEQ ID ND:16)-GG-(LHRH)[a] | | | | |
| 55 | (SEQ ID NO:17)-GG-(LHRH)[a] | | | | |
| 53 | (SEQ ID NO:15)-GG-(LHRH)[a] | N.D. | | 25 μg/dose Alum (0, 3 wpi) | 6/6 |
| 56 | (SEQ ID NO:18)-GG-(LHRH)[a] | | | | |
| 57 | (Inv)[b]-GG-(SEQ ID NO:15)-GG-(LHRH)[a] | N.D. | | 25 μg/dose Alum (0, 3 wpi) | 6/6 |
| 58 | (Inv)[b]-GG-(SEQ ID NO:18)-GG-(LHRH)[a] | | | | |
| 59 | (SEQ ID NO:19)-GG-(LHRH)[a] | 100 μg/dose IFA (0, 3, 6 wpi) | 6/6 | 25 μg/dose Alum (0, 3 wpi) | 14/14 |
| 106 | (SEQ ID NO:105)-GG-(LHRH)[a] | | | | |
| 53 | (SEQ ID NO:15)-GG-(LHRH)[a] | N.D. | | 25 μg/dose Alum (0, 3 wpi) | 1/6 |
| 60 | (Inv)[b]-(SEQ ID NO:15)-GG-(LHRH)[a] | N.D. | | 25 μg/dose Alum (0, 3 wpi) | 4/6 |
| 61 | (SEQ ID NO:20)-GG-(LHRH)[a] | N.D. | | 25 μg/dose Alum (0, 3 wpi) | 4/6 |
| 62 | (Inv)[b]-GG-(SEQ ID NO:20)-GG-(LHRH)[a] | N.D. | | 25 μg/dose Alum (0, 3 wpi) | 2/6 |
| 63 | (Inv)-(SEQ ID NO:21)-GG-(LHRH)[a] | N.D. | | 25 μg/dose Alum (0, 3 wpi) | 1/6 |
| 64 | (SEQ ID NO:22)-GG-(LHRH)[a] | N.D. | | 25 μg/dose Alum (0, 3 wpi) | 4/6 |
| b. HBsAg Th Derivatives | | | | | |
| 65 | (SEQ ID NO:23)-GG-(LHRH)[a] | 400 μg/dose IFA (0, 3, 6 wpi) | 10/10 | 400 μg/dose Alum (0, 3, 6 wpi) | 0/5 |
| 66 | (SEQ ID NO:26)-GG-(LHRH)[a] | 400 μg/dose IFA (0, 3, 6 wpi) | 9/10 | 400 μg/dose Alum (0, 3, 6 wpi) | 2/5 |
| 67 | (SEQ ID NO:27)-GG-(LHRH)[a] | | | | |
| 68 | (SEQ ID NO:28)-GG-(LHRH)[a] | | | | |
| 69 | (SEQ ID ND:29)-GG-(LHRH)[a] | | | | |
| 70 | (SEQ ID NO:30)-GG-(LHRH)[a] | | | | |
| 71 | (SEQ ID NO:31)-GG-(LHRH)[a] | N.D. | | 25 μg/dose Alum (0, 3 wpi) | 8/8 |
| 72 | (SEQ ID NO:32)-GG-(LHRH)[a] | N.D. | | 25 μg/dose Alum (0, 3 wpi) | 4/6 |
| 73 | (SEQ ID NO:33)-GG-(LHRH)[a] | 100 μg/dose IFA (0, 3, 6 wpi) | 4/6 | 25 μg/dose Alum (0, 3 wpi) | 0/6 |
| 74 | (SEQ ID NO:34)-GG-(LHRH)[a] | 100 μg/dose IFA (0, 3, 6 wpi) | 6/6 | 25 μg/dose Alum (0, 3 wpi) | 5/8 |
| 75 | (Inv)[b]-GG-(SEQ ID NO:34)-GG-(LHRH)[a] | N.D. | | 25 μg/dose Alum (0, 3 wpi) | 4/6 |
| 76 | (SEQ ID NO:35)-GG-(LHRH)[a] | N.D. | | 25 μg/dose Alum (0, 3 wpi) | 0/8 |
| | KLH[c]-(LHRH)[a] | N.D. | | 50 μg/dose Alum (0, 3 wpi) | 2/8 |

[a]LHRH = EHWSYGLRPG (SEQ ID NO:77)
[b]INV = Invasin domain (SEQ ID NO:78)
[c]KLH = Keyhole limpet hemocyanin
[d]Hinge spacer = PPXPXP (SEQ ID NO:79)

TABLE 3

Evaluation of Antibody Specificity for the Target Antigenic Site

| SEQ ID NO: | LHRH Reactivity[a] | Th Reactivity[b] |
|---|---|---|
| 41 | 6/6 | 0/6[c] |
| 50 | 8/8 | 0/8[d] |
| 53 | 4/8 | 0/8[e] |

[a]Number of animals with anti-LHRH titers > 1:1000/total animals immunized. The ELISA peptide was SEQ ID NO:28.

[b]Number of animals with anti-Th reactivity > 0.100 $A_{490}$/ total animals immunized. Sera were diluted 1:100 and all $A_{490}$ values were at background values for the respective Th peptides.

[c]ELISA peptide was SEQ ID NO:11.

[d]ELISA peptide was SEQ ID NO:21.

[e]ELISA peptide was SEQ ID NO:24.

TABLE 4

Evaluation of Artificial Th/LHRH Peptide Compositions Including Mixture

| Immunogen[a] | 0 wpi | 5 wpi | 8 wpi | 10 wpi | 14 wpi | 18 wpi | 22 wpi |
|---|---|---|---|---|---|---|---|
| SEQ ID NO: 49 + Alum | 0/8[b] | 3/8 | 8/8 | 8/8 | 7/8 | 5/8 | 3/8 |
| SEQ ID NO: 42 + Alum | 0/6 | 6/6 | 6/6 | 6/6 | 6/6 | 6/6 | 6/6 |
| SEQ ID NO: 49 + SEQ ID NO: 42 + Alum | 0/6 | 6/6 | 6/6 | 6/6 | 6/6 | 6/6 | 6/6 |

[a]Individual LHRH peptide compositions or the mixed LHRH peptide composition were formulated on alum. Immunization schedule: 25 μg/dose at 0 and 3 wpi.

[b]Number of animals immunocastrated/total number of animals in group. Animals were scored as immunocastrated when serum testosterone values were <0.1 nmol/L to undetectable.

We claim:

1. A peptide immunogen represented by the formula:

```
(A)n-(Target antigenic site)-(B)o-(Th)m-X
```
or
```
(A)n-(B)o-(Th)m-(B)o-(Target antigenic site)-X
```
or
```
(A)n-(Th)m-(B)o-(Target antigenic site)-X
```
or
```
(Target antigenic site)-(B)o-(Th)m-(A)n-X
```
or
```
(Th)m-(B)o-(Target antigenic site)-(A)n-X
``` wherein:
   A is an amino acid or a general immunostimulatory sequence, where n is more than one, the individual A's may be the same or different;
   B is selected from the group consisting of amino acids, —HCH(X)CH$_2$SCH$_2$CO—, —NHCH(X)CH$_2$SCH$_2$CO($\epsilon$-N)Lys-, —NHCH(X)CH$_2$S-succinimidyl($\epsilon$-N)Lys-, and —NHCH(X)CH$_2$S-(succinimidyl)-;
   Th is an artificial helper T cell epitope selected from the group consisting of SEQ ID NOS:6–22, 31–35 and 105;
   "Target antigenic site" is LHRH or a homolog thereof from another mammalian species;
   X is an amino acid α-COOH —CONH$_2$;
   n is from 0 to about 10;
   m is from 1 to about 4; and
   o is from 0 to about 10.

2. A peptide immunogen according to claim 1 wherein the immunostimulatory sequence is SEQ ID NO:78.

3. A peptide immunogen according to claim 1 wherein B is selected from the group consisting of Gly-Gly, Pro-Pro-Xaa-Pro-Pro, —NHCH(X)CH$_2$SCH$_2$CO—, —NHCH(X)CH$_2$SCH$_2$CO($\epsilon$-N)Lys-, —NHCH(X)CH$_2$S-succinimidyl ($\epsilon$-N) Lys-, and —NHCH (X)CH$_2$S-(succinimidyl)-.

4. A peptide immunogen according to claim 2 wherein B is selected from the group consisting of Gly-Gly, Pro-Pro-Xaa-Pro-Pro, —NHCH(X)CH$_2$SCH$_2$CO—, —NHCH(X)CH$_2$SCH$_2$CO($\epsilon$-N) Lys-, —NHCH(X)CH$_2$S-succinimidyl ($\epsilon$-N)Lys-, and —NHCH(X)CH$_2$S(succinimidyl)-.

5. A peptide immunogen according to claim 1 wherein B is Gly-Gly.

6. A peptide immunogen according to claim 2 wherein B is Gly-Gly.

7. A peptide immunogen according to claims 1 or 5 selected from the group consisting of SEQ ID NOS: 41–43, 49, 51, 53–56, 59, 61, 64 and 106.

8. A peptide immunogen according to claim 7 selected from the group consisting of SEQ ID NOS: 49, 51, 53–56, 59, 61, 64 and 106.

9. A peptide immunogen according to claims 2 or 6 selected from the group consisting of SEQ ID NOS: 45, 46, 52, 57, 58, 60, 62 and 63.

10. A peptide immunogen according to claim 9 selected from the group consisting of SEQ ID NOS: 45, 46, 52, 57, 58 and 60.

11. A pharmaceutical composition comprising an immunologically effective amount of a peptide immunogen of any one of claims 1–6 further comprising a pharmaceutically acceptable carrier.

12. A pharmaceutical composition comprising an immunologically effective amount of a peptide immunogen of claim 7 further comprising a pharmaceutically acceptable carrier.

13. A pharmaceutical composition comprising an immunologically effective amount of a peptide immunogen of claim 8 further comprising a pharmaceutically acceptable carrier.

14. A pharmaceutical composition according to claim 11, wherein said immunologically effective amount of said peptide or peptide conjugate is between about 0.5 μg and about 1 mg per kilogram body weight per dose.

15. A pharmaceutical composition according to claim 12, wherein said immunologically effective amount of said peptide or peptide conjugate is between about 0.5 μg and about 1 mg per kilogram body weight per dose.

16. A pharmaceutical composition according to claim 13, wherein said immunologically effective amount of said peptide or peptide conjugate is between about 0.5 μg and about 1 mg per kilogram body weight per dose.

* * * * *

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (xi) SEQUENCE DESCRIPTION: SEQ ID NO:1:

```
Leu Ser Glu Ile Lys Gly Val Ile Val His Arg Leu
1               5                   10
Glu Gly Val
        15
```

(2) INFORMATION FOR SEQ ID NO:2:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (xi) SEQUENCE DESCRIPTION: SEQ ID NO:2:

```
Asp Leu Ser Asp Leu Lys Gly Leu Leu Leu His Lys
1               5                   10
Leu Asp Gly Leu
        15
```

(2) INFORMATION FOR SEQ ID NO:3:

(i) SEQUENCE CHARACTERISTICS:
      (A) LENGTH: 16 amino acids
      (B) TYPE: amino acid (C) TOPOLOGY: LINEAR (ii) MOLECULE TYPE: peptide (xi) SEQUENCE DESCRIPTION: SEQ ID NO:3:

Glu Ile Ser Glu Ile Arg Gly Ile Ile Ile His Arg
1               5                   10

Ile Glu Gly Ile
        15

(2) INFORMATION FOR SEQ ID NO:4:

(i) SEQUENCE CHARACTERISTICS:
            (A) LENGTH: 16 amino acids
            (B) TYPE: amino acid
            (C) TOPOLOGY: LINEAR (ii) MOLECULE TYPE: peptide (xi) SEQUENCE DESCRIPTION: SEQ ID NO:4:

Asp Val Ser Asp Val Lys Gly Val Val Val His
1               5                   10

Lys Val Asp Gly Val
        15

(2) INFORMATION FOR SEQ ID NO:5:

(i) SEQUENCE CHARACTERISTICS:
            (A) LENGTH: 16 amino acids
            (B) TYPE: amino acid
            (C) TOPOLOGY: LINEAR (ii) MOLECULE TYPE: peptide (xi) SEQUENCE DESCRIPTION: SEQ ID NO:5:

Asp Phe Ser Asp Phe Lys Gly Phe Phe Phe His
1               5                   10

Lys Phe Asp Gly Phe
        15

(2) INFORMATION FOR SEQ ID NO:6:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION:SEQ ID NO:6:

Ile Ser Glu Ile Lys Gly Val Ile Val His Lys Ile
1               5                   10

Glu Gly Ile
        15

(2) INFORMATION FOR SEQ ID NO:7:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO: 7:

```
Met Thr Glu Ile Arg Thr Val Ile Val Thr Arg Met
1               5                   10

Glu Thr Met
        15

(2) INFORMATION FOR SEQ ID NO:8:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:8:

Leu Ser Glu Ile Lys Gly Val Ile Val His Lys Leu
1               5                   10

Glu Gly Val
        15

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:9:

Ile Thr Glu Ile Arg Thr Val Ile Val Thr Arg Ile
1               5                   10

Glu Thr Ile
        15

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:10:

Met Ser Glu Ile Lys Gly Val Ile Val His Lys Leu
1               5                   10

Glu Gly Met
        15

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:11:

Leu Thr Glu Met Arg Thr Val Ile Val Thr Arg Met
1               5                   10

Glu Thr Val
        15
```

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:12:

```
Ile Thr Glu Ile Arg Thr Val Ile Val Thr Arg Ile
1               5                   10
Glu Thr Ile
        15
```

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:13:

```
Met Ser Glu Met Lys Gly Val Ile Val His Lys Met
1               5                   10
Glu Gly Met
        15
```

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:14:

```
Leu Thr Glu Ile Arg Thr Val Ile Val Thr Arg Leu
1               5                   10
Glu Thr Val
        15
```

(2) INFORMATION FOR SEQ ID NO:15:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:15:

```
Ile Ser Ile Ser Glu Ile Lys Gly Val Ile Val His
1               5                   10
Lys Ile Glu Gly Ile Leu Phe
        15
```

(2) INFORMATION FOR SEQ ID NO:16:

(i) SEQUENCE CHARACTERISTICS:
        (A) LENGTH: 19 amino acids
        (B) TYPE: amino acid
        (D) TOPOLOGY: linear

```
        (ii) MOLECULE TYPE: peptide (xi) SEQUENCE DESCRIPTION: SEQ ID NO:16:

Ile Ser Met Thr Glu Ile Arg Thr Val Ile Val Thr
1               5                   10

Arg Met Glu Thr Met Leu Phe
            15

(2) INFORMATION FOR SEQ ID NO:17:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (xi) SEQUENCE DESCRIPTION: SEQ ID NO:17:

Ile Ser Leu Ser Glu Ile Lys Gly Val Ile Val His
1               5                   10

Lys Leu Glu Gly Val Leu Phe
            15

(2) INFORMATION FOR SEQ ID NO:18:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (xi) SEQUENCE DESCRIPTION: SEQ ID NO:18:

Ile Ser Ile Thr Glu Ile Arg Thr Val Ile Val Thr
1               5                   10

Arg Ile Glu Thr Ile Leu Phe
            15

(2) INFORMATION FOR SEQ ID NO:19:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (xi) SEQUENCE DESCRIPTION: SEQ ID NO:19:

Ile Ser Leu Ser Glu Ile Lys Gly Val Ile Val His
1               5                   10

Lys Leu Glu Gly Met Leu Phe
            15

(2) INFORMATION FOR SEQ ID NO:20:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (xi) SEQUENCE DESCRIPTION: SEQ ID NO:20:

Ile Ser Ile Thr Glu Ile Arg Thr Val Ile Val Thr
1               5                   10
```

```
Arg Ile Glu Thr Ile Leu Phe
        15

(2) INFORMATION FOR SEQ ID NO:21:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:21:

Ile Ser Met Ser Glu Met Lys Gly Val Ile Val His
1               5                   10

Lys Met Glu Gly Met Leu Phe
        15

(2) INFORMATION FOR SEQ ID NO:22:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:22:

Ile Ser Leu Thr Glu Ile Arg Thr Val Ile Val Thr
1               5                   10

Arg Leu Glu Thr Val Leu Phe
        15

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:23:

Phe Phe Leu Leu Thr Arg Ile Leu Thr Ile Pro Gln
1               5                   10

Ser Leu Asp
        15

(2) INFORMATION FOR SEQ ID NO:24:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:24:

Lys Lys Lys Phe Phe Leu Leu Thr Arg Ile Leu Thr
1               5                   10

Ile Pro Gln Ser Leu Asp
        15

(2) INFORMATION FOR SEQ ID NO:25:

(i) SEQUENCE CHARACTERISTICS:
```

(A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:25:

Phe Phe Leu Leu Thr Arg Ile Leu Thr Ile Pro Gln
1               5                   10

Ser Leu (2) INFORMATION FOR SEQ ID NO:26:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:26:

Lys Lys Lys Leu Phe Leu Leu Thr Lys Leu Leu Thr
1               5                   10

Leu Pro Gln Ser Leu Asp
            15

(2) INFORMATION FOR SEQ ID NO:27:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:27:

Arg Arg Arg Ile Lys Ile Ile Thr Arg Ile Ile Thr
1               5                   10

Ile Pro Leu Ser Ile Arg
            15

(2) INFORMATION FOR SEQ ID NO:28:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:28:

Lys Lys Lys Val Arg Val Val Thr Lys Val Val Thr
1               5                   10

Val Pro Ile Ser Val Asp
            15

(2) INFORMATION FOR SEQ ID NO:29:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:29:

```
Lys Lys Lys Phe Phe Phe Phe Thr Lys Phe Phe Thr
1               5                   10

Phe Pro Val Ser Phe Asp
        15
```

(2) INFORMATION FOR SEQ ID NO:30:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:30:

```
Lys Lys Lys Leu Phe Leu Leu Thr Lys Leu Leu Thr
1               5                   10

Leu Pro Phe Ser Leu Asp
        15
```

(2) INFORMATION FOR SEQ ID NO:31:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:31:

```
Lys Lys Lys Ile Ile Thr Ile Thr Arg Ile Ile Thr
1               5                   10

Ile Ile Thr Thr Ile Asp
        15
```

(2) INFORMATION FOR SEQ ID NO:32:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:32:

```
Lys Lys Lys Ile Ile Thr Ile Thr Arg Ile Ile Thr
1               5                   10

Ile Ile Thr Thr Ile
        15
```

(2) INFORMATION FOR SEQ ID NO:33:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:33:

```
Lys Lys Lys Met Met Thr Met Thr Arg Met Ile Thr
1               5                   10

Met Ile Thr Thr Ile Asp
        15
```

```
(2)  INFORMATION FOR SEQ ID NO:34:

(i) SEQUENCE CHARACTERISTICS:
           (A) LENGTH: 16 amino acids
           (B) TYPE: amino acid
           (D) TOPOLOGY: linear (ii) MOLECULE TYPE: peptide (xi) SEQUENCE DESCRIPTION: SEQ ID NO:34:

Phe Ile Thr Met Asp Thr Lys Phe Leu Leu Ala Ser
 1               5                  10

Thr His Ile Leu
        15

(2)  INFORMATION FOR SEQ ID NO:35:

(i) SEQUENCE CHARACTERISTICS:
           (A) LENGTH: 19 amino acids
           (B) TYPE: amino acid
           (D) TOPOLOGY: linear (ii) MOLECULE TYPE: peptide (xi) SEQUENCE DESCRIPTION: SEQ ID NO:35:

Lys Lys Lys Phe Ile Thr Met Asp Thr Lys Phe Leu
 1               5                  10

Leu Ala Ser Thr His Ile Leu
        15

(2)  INFORMATION FOR SEQ ID NO:36:

(i) SEQUENCE CHARACTERISTICS:
           (A) LENGTH: 27 amino acids
           (B) TYPE: amino acid
           (D) TOPOLOGY: linear (ii) MOLECULE TYPE: peptide (xi) SEQUENCE DESCRIPTION: SEQ ID NO:36:

Leu Ser Glu Ile Lys Gly Val Ile Val His Arg Leu
 1               5                  10

Glu Gly Val Gly Gly Glu His Trp Ser Tyr Gly Leu
        15                  20

Arg Pro Gly
25

(2)  INFORMATION FOR SEQ ID NO:37:

(i) SEQUENCE CHARACTERISTICS:
           (A) LENGTH: 28 amino acids
           (B) TYPE: amino acid
           (D) TOPOLOGY: linear (ii) MOLECULE TYPE: peptide (xi) SEQUENCE DESCRIPTION: SEQ ID NO:37:

Asp Leu Ser Asp Leu Lys Gly Leu Leu Leu His Lys
 1               5                  10

Leu Asp Gly Leu Gly Gly Glu His Trp Ser Tyr Gly
        15                  20

Leu Arg Pro Gly
25

(2)  INFORMATION FOR SEQ ID NO:38:
```

```
        (i) SEQUENCE CHARACTERISTICS:
             (A) LENGTH: 28 amino acids
             (B) TYPE: amino acid
             (D) TOPOLOGY: linear (ii) MOLECULE TYPE: peptide (xi) SEQUENCE DESCRIPTION: SEQ ID NO:38:

Glu Ile Ser Glu Ile Arg Gly Ile Ile Ile His Arg
1               5                   10

Ile Glu Gly Ile Gly Gly Glu His Trp Ser Tyr Gly
            15                  20

Leu Arg Pro Gly
25

(2) INFORMATION FOR SEQ ID NO:39:

(i) SEQUENCE CHARACTERISTICS:
             (A) LENGTH: 28 amino acids
             (B) TYPE: amino acid
             (D) TOPOLOGY: linear (ii) MOLECULE TYPE: peptide (xi) SEQUENCE DESCRIPTION: SEQ ID NO:39:

Asp Val Ser Asp Val Lys Gly Val Val Val His Lys
1               5                   10

Val Asp Gly Val Gly Gly Glu His Trp Ser Tyr Gly
            15                  20

Leu Arg Pro Gly
25

(2) INFORMATION FOR SEQ ID NO:40:

(i) SEQUENCE CHARACTERISTICS:
             (A) LENGTH: 28 amino acids
             (B) TYPE: amino acid
             (D) TOPOLOGY: linear (ii) MOLECULE TYPE: peptide (xi) SEQUENCE DESCRIPTION: SEQ ID NO:40:

Asp Phe Ser Asp Phe Lys Gly Phe Phe Phe His Lys
1               5                   10

Phe Asp Gly Phe Gly Gly Glu His Trp Ser Tyr
            15                  20

Gly Leu Arg Pro Gly
25

(2) INFORMATION FOR SEQ ID NO:41:

(i) SEQUENCE CHARACTERISTICS:
             (A) LENGTH: 27 amino acids
             (B) TYPE: amino acid
             (D) TOPOLOGY: linear (ii) MOLECULE TYPE: peptide (xi) SEQUENCE DESCRIPTION: SEQ ID NO:41:

Ile Ser Glu Ile Lys Gly Val Ile Val His Lys Ile
1               5                   10

Glu Gly Ile Gly Gly Glu His Trp Ser Tyr Gly Leu
            15                  20
```

```
Arg Pro Gly
25
```

(2) INFORMATION FOR SEQ ID NO:42:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:42:

```
Met Thr Glu Ile Arg Thr Val Ile Val Thr Arg Met
1               5                   10

Glu Thr Met Gly Gly Glu His Trp Ser Tyr Gly Leu
            15                  20

Arg Pro Gly
25
```

(2) INFORMATION FOR SEQ ID NO:43:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:43:

```
Leu Ser Glu Ile Lys Gly val Ile Val His Lys Leu
1               5                   10

Glu Gly Val Gly Gly Glu His Trp Ser Tyr Gly Leu
            15                  20

Arg Pro Gly
25
```

(2) INFORMATION FOR SEQ ID NO:44:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:44:

```
Ile Thr Glu Ile Arg Thr Val Ile Val Thr Arg Ile
1               5                   10

Glu Thr Ile Gly Gly Glu His Trp Ser Tyr Gly Leu
            15                  20

Arg Pro Gly
25
```

(2) INFORMATION FOR SEQ ID NO:45:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:45:

```
Thr Ala Lys Ser Lys Lys Phe Pro Ser Tyr Thr Ala
```

```
1               5                   10
Thr Tyr Gln Phe Gly Gly Ile Ser Glu Ile Lys Gly
            15                  20

Val Ile Val His Lys Ile Glu Gly Ile Gly Gly Glu
25                  30                  35

His Trp Ser Tyr Gly Leu Arg Pro Gly
            40                  45
```

(2) INFORMATION FOR SEQ ID NO:46:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:46:

```
Thr Ala Lys Ser Lys Lys Phe Pro Ser Tyr Thr Ala
1               5                   10

Thr Tyr Gln Phe Gly Gly Ile Thr Glu Ile Arg Thr
            15                  20

Val Ile Val Thr Arg Ile Glu Thr Ile Gly Gly Glu
25                  30                  35

His Trp Ser Tyr Gly Leu Arg Pro Gly
            40
```

(2) INFORMATION FOR SEQ ID NO:47:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:47:

```
Met Ser Glu Ile Lys Gly Val Ile Val His Lys Leu
1               5                   10

Glu Gly Met Gly Gly Glu His Trp Ser Tyr Gly Leu
            15                  20

Arg Pro Gly
25
```

(2) INFORMATION FOR SEQ ID NO:48:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:48:

```
Leu Thr Glu Met Arg Thr Val Ile Val Thr Arg Met
1               5                   10

Glu Thr Val Gly Gly Glu His Trp Ser Tyr Gly Leu
            15                  20

Arg Pro Gly
25
```

(2) INFORMATION FOR SEQ ID NO:49:

```
        (i) SEQUENCE CHARACTERISTICS:
            (A) LENGTH: 27 amino acids
            (B) TYPE: amino acid
            (D) TOPOLOGY: linear (ii) MOLECULE TYPE: peptide (xi) SEQUENCE DESCRIPTION: SEQ ID NO:49:

Ile Thr Glu Ile Arg Thr Val Ile Val Thr Arg Ile
1               5                   10

Glu Thr Ile Gly Gly Glu His Trp Ser Tyr Gly Leu
            15                  20

Arg Pro Gly
25

(2) INFORMATION FOR SEQ ID NO:50:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (xi) SEQUENCE DESCRIPTION: SEQ ID NO:50:

Met Ser Glu Met Lys Gly Val Ile Val His Lys Met
1               5                   10

Glu Gly Met Gly Gly Glu His Trp Ser Tyr Gly Leu
            15                  20

Arg Pro Gly
25

(2) INFORMATION FOR SEQ ID NO:51:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (xi) SEQUENCE DESCRIPTION: SEQ ID NO:51:

Leu Thr Glu Ile Arg Thr Val Ile Val Thr Arg Leu
1               5                   10

Glu Thr Val Gly Gly Glu His Trp Ser Tyr Gly Leu
            15                  20

Arg Pro Gly
25

(2) INFORMATION FOR SEQ ID NO:52:

(i) SEQUENCE CHARACTERISTICS:
            (A) LENGTH: 45 amino acids
            (B) TYPE: amino acid
            (D) TOPOLOGY: linear (ii) MOLECULE TYPE: peptide (xi) SEQUENCE DESCRIPTION: SEQ ID NO:52:

Thr Ala Lys Ser Lys Lys Phe Pro Ser Tyr Thr Ala
1               5                   10

Thr Tyr Gln Phe Gly Gly Leu Thr Glu Ile Arg Thr
            15                  20
```

```
Val Ile Val Thr Arg Leu Glu Thr Val Gly Gly Glu
 25                  30                  35

His Trp Ser Tyr Gly Leu Arg Pro Gly
             40                  45
```

(2) INFORMATION FOR SEQ ID NO:53:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:53:

```
Ile Ser Ile Ser Glu Ile Lys Gly Val Ile Val His
 1               5                  10

Lys Ile Glu Gly Ile Leu Phe Gly Gly Glu His Trp
             15                  20

Ser Tyr Gly Leu Arg Pro Gly
 25                  30
```

(2) INFORMATION FOR SEQ ID NO:54:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:54:

```
Ile Ser Met Thr Glu Ile Arg Thr Val Ile Val Thr
 1               5                  10

Arg Met Glu Thr Met Leu Phe Gly Gly Glu His Trp
             15                  20

Ser Tyr Gly Leu Arg Pro Gly
 25                  30
```

(2) INFORMATION FOR SEQ ID NO:55:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:55:

```
Ile Ser Leu Ser Glu Ile Lys Gly Val Ile Val His
 1               5                  10

Lys Leu Glu Gly Val Leu Phe Gly Gly Glu His Trp
             15                  20

Ser Tyr Gly Leu Arg Pro Gly
 25                  30
```

(2) INFORMATION FOR SEQ ID NO:56:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:56:

Ile Ser Ile Thr Glu Ile Arg Thr Val Ile Val Thr
 1               5                  10

Arg Ile Glu Thr Ile Leu Phe Gly Gly Glu His Trp
            15                  20

Ser Tyr Gly Leu Arg Pro Gly
 25                  30

(2) INFORMATION FOR SEQ ID NO:57:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (xi) SEQUENCE DESCRIPTION: SEQ ID NO:57:

Thr Ala Lys Ser Lys Lys Phe Pro Ser Tyr Thr Ala
 1               5                  10

Thr Tyr Gln Phe Gly Gly Ile Ser Ile Ser Glu Ile
            15                  20

Lys Gly Val Ile Val His Lys Ile Glu Gly Ile Leu
 25                  30                  35

Phe Gly Gly Glu His Trp Ser Tyr Gly Leu Arg Pro
                 40                  45

Gly (2) INFORMATION FOR SEQ ID NO:58:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (xi) SEQUENCE DESCRIPTION: SEQ ID NO:58:

Thr Ala Lys Ser Lys Lys Phe Pro Ser Tyr Thr Ala
 1               5                  10

Thr Tyr Gln Phe Gly Gly Ile Ser Ile Thr Glu Ile
            15                  20

Arg Thr Val Ile Val Thr Arg Ile Glu Thr Ile Leu
 25                  30                  35

Phe Gly Gly Glu His Trp Ser Tyr Gly Leu Arg Pro
                 40                  45

Gly (2) INFORMATION FOR SEQ ID NO:59:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:59:

Ile Ser Leu Ser Glu Ile Lys Gly Val Ile Val His
 1               5                  10

Lys Leu Glu Gly Met Leu Phe Gly Gly Glu His Trp

```
            15                  20
Ser Tyr Gly Leu Arg Pro Gly
 25                  30

(2) INFORMATION FOR SEQ ID NO:60:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:60:

Thr Ala Lys Ser Lys Lys Phe Pro Ser Tyr Thr Ala
 1               5                  10

Thr Tyr Gln Phe Ile Ser Ile Ser Glu Ile Lys Gly
            15                  20

Val Ile Val His Lys Ile Glu Gly Ile Leu Phe Gly
 25                  30                  35

Gly Glu His Trp Ser Tyr Gly Leu Arg Pro Gly
                40                  45

(2) INFORMATION FOR SEQ ID NO:61:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:61:

Ile Ser Ile Thr Glu Ile Arg Thr Val Ile Val Thr
 1               5                  10

Arg Ile Glu Thr Ile Leu Phe Gly Gly Glu His Trp
            15                  20

Ser Tyr Gly Leu Arg Pro Gly
 25                  30

(2) INFORMATION FOR SEQ ID NO:62:

(i) SEQUENCE CHARACTERISTICS:
        (A) LENGTH: 49 amino acids
        (B) TYPE: amino acid
        (D) TOPOLOGY: linear (ii) MOLECULE TYPE: peptide (xi) SEQUENCE DESCRIPTION: SEQ ID NO:62:

Thr Ala Lys Ser Lys Lys Phe Pro Ser Tyr Thr Ala
 1               5                  10

Thr Tyr Gln Phe Gly Gly Ile Ser Ile Thr Glu Ile
            15                  20

Arg Thr Val Ile Val Thr Arg Ile Glu Thr Ile Leu
 25                  30                  35

Phe Gly Gly Glu His Trp Ser Tyr Gly Leu Arg Pro
                40                  45

Gly (2) INFORMATION FOR SEQ ID NO:63:
```

(i) SEQUENCE CHARACTERISTICS:
            (A) LENGTH: 47 amino acids
            (B) TYPE: amino acid
            (D) TOPOLOGY: linear (ii) MOLECULE TYPE: peptide (xi) SEQUENCE DESCRIPTION: SEQ ID NO:63:

Thr Ala Lys Ser Lys Phe Pro Ser Tyr Thr Ala
1               5                  10

Thr Tyr Gln Phe Ile Ser Met Ser Glu Met Lys Gly
            15                  20

Val Ile Val His Lys Met Glu Gly Met Leu Phe Gly
25                  30                  35

Gly Glu His Trp Ser Tyr Gly Leu Arg Pro Gly
                40                  45

(2) INFORMATION FOR SEQ ID NO:64:

(i) SEQUENCE CHARACTERISTICS:
            (A) LENGTH: 31 amino acids
            (B) TYPE: amino acid
            (D) TOPOLOGY: linear (ii) MOLECULE TYPE: peptide (xi) SEQUENCE DESCRIPTION: SEQ ID NO:64:

Ile Ser Leu Thr Glu Ile Arg Thr Val Ile Val Thr
1               5                  10

Arg Leu Glu Thr Val Leu Phe Gly Gly Glu His Trp
            15                  20

Ser Tyr Gly Leu Arg Pro Gly
25                  30

(2) INFORMATION FOR SEQ ID NO:65:

(i) SEQUENCE CHARACTERISTICS:
            (A) LENGTH: 27 amino acids
            (B) TYPE: amino acid
            (D) TOPOLOGY: linear (ii) MOLECULE TYPE: peptide (xi) SEQUENCE DESCRIPTION: SEQ ID NO:65:

Phe Phe Leu Leu Thr Arg Ile Leu Thr Ile Pro Gln
1               5                  10

Ser Leu Asp Gly Gly Glu His Trp Ser Tyr Gly Leu
            15                  20

Arg Pro Gly
25

(2) INFORMATION FOR SEQ ID NO:66:

(i) SEQUENCE CHARACTERISTICS:
            (A) LENGTH: 30 amino acids
            (B) TYPE: amino acid
            (D) TOPOLOGY: linear (ii) MOLECULE TYPE: peptide (xi) SEQUENCE DESCRIPTION: SEQ ID NO:66:

Lys Lys Lys Leu Phe Leu Leu Thr Lys Leu Leu Thr
1               5                  10

Leu Pro Gln Ser Leu Asp Gly Gly Glu His Trp Ser

```
                     15                  20

Tyr Gly Leu Arg Pro Gly
25                  30

(2) INFORMATION FOR SEQ ID NO:67:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:67:

Arg Arg Arg Ile Lys Ile Ile Thr Arg Ile Ile Thr
1               5                  10

Ile Pro Leu Ser Ile Arg Gly Gly Glu His Trp Ser
                15                  20

Tyr Gly Leu Arg Pro Gly
25                  30

(2) INFORMATION FOR SEQ ID NO:68:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:68:

Lys Lys Lys Val Arg Val Val Thr Lys Val Val Thr
1               5                  10

Val Pro Ile Ser Val Asp Gly Gly Glu His Trp Ser
                15                  20

Tyr Gly Leu Arg Pro Gly
25

(2) INFORMATION FOR SEQ ID NO:69:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:69:

Lys Lys Lys Phe Phe Phe Phe Thr Lys Phe Phe Thr
1               5                  10

Phe Pro Val Ser Phe Asp Gly Gly Glu His Trp Ser
                15                  20

Tyr Gly Leu Arg Pro Gly
25                  30

(2) INFORMATION FOR SEQ ID NO:70:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:70:
```

Lys Lys Lys Leu Phe Leu Leu Thr Lys Leu Leu Thr
1               5                  10

Leu Pro Phe Ser Leu Asp Gly Gly Glu His Trp Ser
            15                  20

Tyr Gly Leu Arg Pro Gly
25              30

(2) INFORMATION FOR SEQ ID NO:71:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:71:

Lys Lys Lys Ile Ile Thr Ile Thr Arg Ile Ile Thr
1               5                  10

Ile Ile Thr Thr Ile Asp Gly Gly Glu His Trp Ser
            15                  20

Tyr Gly Leu Arg Pro Gly
25              30

(2) INFORMATION FOR SEQ ID NO:72:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (xi) SEQUENCE DESCRIPTION: SEQ ID NO:72:

Lys Lys Lys Ile Ile Thr Ile Thr Arg Ile Ile Thr
1               5                  10

Ile Ile Thr Thr Ile Gly Gly Glu His Trp Ser Tyr
            15                  20

Gly Leu Arg Pro Gly
25

(2) INFORMATION FOR SEQ ID NO:73:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:73:

Lys Lys Lys Met Met Thr Met Thr Arg Met Ile Thr
1               5                  10

Met Ile Thr Thr Ile Asp Gly Gly Glu His Trp Ser
            15                  20

Tyr Gly  Leu Arg Pro Gly
25               30

(2) INFORMATION FOR SEQ ID NO:74:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:74:

Phe Ile Thr Met Asp Thr Lys Phe Leu Leu Ala Ser
1               5                  10

Thr His Ile Leu Gly Gly Glu His Trp Ser Tyr Gly
            15                  20

Leu Arg Pro Gly
25

(2) INFORMATION FOR SEQ ID NO:75:

(i) SEQUENCE CHARACTERISTICS:
            (A) LENGTH: 46 amino acids
            (B) TYPE: amino acid
            (D) TOPOLOGY: linear (ii) MOLECULE TYPE: peptide (xi) SEQUENCE DESCRIPTION: SEQ ID NO:75:

Thr Ala Lys Ser Lys Phe Pro Ser Tyr Thr Ala
1               5                  10

Thr Tyr Gln Phe Gly Gly Phe Ile Thr Met Asp Thr
            15                  20

Lys Phe Leu Leu Ala Ser Thr His Ile Leu Gly Gly
25                  30                  35

Glu His Trp Ser Tyr Gly Leu Arg Pro Gly
                40                  45

(2) INFORMATION FOR SEQ ID NO:76:

(i) SEQUENCE CHARACTERISTICS:
            (A) LENGTH: 31 amino acids
            (B) TYPE: amino acid
            (D) TOPOLOGY: linear (ii) MOLECULE TYPE: peptide (xi) SEQUENCE DESCRIPTION: SEQ ID NO:76:

Lys Lys Lys Phe Ile Thr Met Asp Thr Lys Phe Leu
1               5                  10

Leu Ala Ser Thr His Ile Leu Gly Gly Glu His Trp
            15                  20

Ser Tyr Gly Leu Arg Pro Gly
25                  30

(2) INFORMATION FOR SEQ ID NO:77:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:77:

Glu His Trp Ser Tyr Gly Leu Arg Pro Gly
1               5                  10

(2) INFORMA ON FOR SEQ ID NO:78:

(i) SEQUENCE CHARACTERISTICS:
            (A LENGTH: 16 amino acids

```
            (B) TYPE: amino acid
            (D) TOPOLOGY: linear (ii) MOLECULE TYPE: peptide (xi) SEQUENCE DESCRIPTION: SEQ ID NO:78:

Thr Ala Lys Ser Lys Lys Phe Pro Ser Tyr Thr Ala
1               5                  10

Thr Tyr Gln Phe
            15

(2) INFORMATION FOR SEQ ID NO:79:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO:79:

Pro Pro Xaa Pro Xaa Pro
1               5

(2) INFORMATION FOR SEQ ID NO:80:

(i) SEQUENCE CHARACTERISTICS:
            (A) LENGTH: 35 amino acids
            (B) TYPE: amino acid
            (D) TOPOLOGY: linear (ii) MOLECULE TYPE: peptide (xi) SEQUENCE DESCRIPTION: SEQ ID NO:80:

Ile Ser Ile Ser Glu Ile Lys Gly Val Ile Val His
1               5                  10

Lys Ile Glu Gly Ile Leu Phe Pro Pro Xaa Pro Xaa
            15                  20

Pro Glu His Trp Ser Tyr Gly Leu Arg Pro Gly
25                  30                  35

(2) INFORMATION FOR SEQ ID NO:81:

(i) SEQUENCE CHARACTERISTICS:
            (A) LENGTH: 35 amino acids
            (B) TYPE: amino acid
            (D) TOPOLOGY: linear (ii) MOLECULE TYPE: peptide (xi) SEQUENCE DESCRIPTION: SEQ ID NO:81:

Ile Ser Ile Thr Glu Ile Arg Thr Val Ile Val Thr
1               5                  10

Arg Ile Glu Thr Ile Leu Phe Pro Pro Xaa Pro Xaa
            15                  20

Pro Glu His Trp Ser Tyr Gly Leu Arg Pro Gly
25                  30                  35

(2) INFORMATION FOR SEQ ID NO:82:

(i) SEQUENCE CHARACTERISTICS:
            (A) LENGTH: 34 amino acids
            (B) TYPE: amino acid
            (D) TOPOLOGY: linear (ii) MOLECULE TYPE: peptide
```

(xi) SEQUENCE DESCRIPTION: SEQ ID NO:82:

Lys Lys Lys Ile Ile Thr Ile Thr Arg Ile Ile Thr
1               5                   10

Ile Ile Thr Thr Ile Asp Pro Pro Xaa Pro Xaa Pro
            15                  20

Glu His Trp Ser Tyr Gly Leu Arg Pro Gly
25                  30

(2) INFORMATION FOR SEQ ID NO:83:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:83:

Ala Gly Cys Lys Asn Phe Phe Trp Lys Thr Phe Thr
1               5                   10

Ser Cys (2) INFORMATION FOR SEQ ID NO:84:

(i) SEQUENCE CHARACTERISTICS:
        (A LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:84:

Ile Ser Glu Ile Lys Gly Val Ile Val His Lys Ile
1               5                   10

Glu Gly Ile Gly Gly Ala Gly Cys Lys Asn Phe Phe
            15                  20

Trp Lys Thr Phe Thr Ser Cys
25                  30

(2) INFORMATION FOR SEQ ID NO:85:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:85:

Met Thr Glu Ile Arg Thr Val Ile Val Thr Arg Met
1               5                   10

Glu Thr Met Gly Gly Ala Gly Cys Lys Asn Phe Phe
            15                  20

Trp Lys Thr Phe Thr Ser Cys
25                  30

(2) INFORMATION FOR SEQ ID NO:86:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:86:

Leu Ser Glu Ile Lys Gly Val Ile Val His Lys Leu
1               5                   10

Glu Gly Val Gly Gly Ala Gly Cys Lys Asn Phe Phe
            15                  20

Trp Lys Thr Phe Thr Ser Cys
25                  30

(2) INFORMATION FOR SEQ ID NO:87:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:87:

Ala Gly Cys Lys Asn Phe Phe Trp Lys Thr Phe Thr
1               5                   10

Ser Cys Gly Gly Ile Ser Glu Ile Lys Gly Val Ile
            15                  20

Val His Lys Ile Glu Gly Ile
25                  30

(2) INFORMATION FOR SEQ ID NO:88:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:88:

Ala Gly Cys Lys Asn Phe Phe Trp Lys Thr Phe Thr
1               5                   10

Ser Cys Gly Gly Met Thr Glu Ile Arg Thr Val Ile
            15                  20

Val Thr Arg Met Gly Thr Met
25                  30

(2) INFORMATION FOR SEQ ID NO:89:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:89:

Ala Gly Cys Lys Asn Phe Phe Trp Lys Thr Phe Thr
1               5                   10

Ser Cys Gly Gly Leu Ser Glu Ile Lys Gly Val Ile
            15                  20

Val His Lys Leu Glu Gly Val
25                  30

(2) INFORMATION FOR SEQ ID NO:90:

```
     (i) SEQUENCE CHARACTERISTICS:
         (A) LENGTH: 34 amino acids
         (B) TYPE: amino acid
         (D) TOPOLOGY: linear (ii) MOLECULE TYPE: peptide (xi) SEQUENCE DESCRIPTION: SEQ ID NO:90:

Lys Lys Lys Ile Ile Thr Ile Thr Arg Ile Ile Thr
1               5                   10

Ile Ile Thr Thr Ile Asp Gly Gly Ala Gly Cys Lys
            15                  20

Asn Phe Phe Trp Lys Thr Phe Thr Ser Cys
25                  30

(2) INFORMATION FOR SEQ ID NO:91:

(i) SEQUENCE CHARACTERISTICS:
         (A) LENGTH: 30 amino acids
         (B) TYPE: amino acid
         (D) TOPOLOGY: linear (ii) MOLECULE TYPE: peptide (xi) SEQUENCE DESCRIPTION: SEQ ID NO:91:

Cys Asn Gln Gly Ser Phe Leu Thr Lys Gly Pro Ser
1               5                   10

Lys Leu Asn Asp Arg Ala Asp Ser Arg Arg Ser Leu
            15                  20

Trp Asp Gln Gly Asn Cys
25                  30

(2) INFORMATION FOR SEQ ID NO:92:

(i) SEQUENCE CHARACTERISTICS:
         (A) LENGTH: 47 amino acids
         (B) TYPE: amino acid
         (D) TOPOLOGY: linear (ii) MOLECULE TYPE: peptide (xi) SEQUENCE DESCRIPTION: SEQ ID NO:92:

Ile Ser Glu Ile Lys Gly Val Ile Val His Lys Ile
1               5                   10

Glu Gly Ile Gly Gly Cys Asn Gln Gly Ser Phe Leu
            15                  20

Thr Lys Gly Pro Ser Lys Leu Asn Asp Arg Ala Asp
25                  30                  35

Ser Arg Arg Ser Leu Trp Asp Gln Gly Asn Cys
                40                  45

(2) INFORMATION FOR SEQ ID NO:93:

(i) SEQUENCE CHARACTERISTICS:
         (A) LENGTH: 47 amino acids
         (B) TYPE: amino acid
         (D) TOPOLOGY: linear (ii) MOLECULE TYPE: peptide (xi) SEQUENCE DESCRIPTION: SEQ ID NO:93:

Met Thr Glu Ile Arg Thr Val Ile Val Thr Arg Met
1               5                   10

Glu Thr Met Gly Gly Cys Asn Gln Gly Ser Phe Leu
```

```
              15                  20
Thr Lys Gly Pro Ser Lys Leu Asn Asp Arg Ala Asp
25                  30                  35

Ser Arg Arg Ser Leu Trp Asp Gln Gly Asn Cys
            40                  45

(2) INFORMATION FOR SEQ ID NO:94:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:94:

Leu Ser Glu Ile Lys Gly Val Ile Val His Lys Leu
1               5                   10

Glu Gly Val Gly Gly Cys Asn Gln Gly Ser Phe Leu
            15                  20

Thr Lys Gly Pro Ser Lys Leu Asn Asp Arg Ala Asp
25                  30                  35

Ser Arg Arg Ser Leu Trp Asp Gln Gly Asn Cys
            40                  45

(2) INFORMATION FOR SEQ ID NO:95:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:95:

Cys Gly Glu Thr Tyr Gln Ser Arg Val Thr His Pro
1               5                   10

His Leu Pro Arg Ala Leu Met Arg Ser Thr Thr Lys
            15                  20

Cys
25

(2) INFORMATION FOR SEQ ID NO:96:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:96:

Ile Ser Ile Ser Glu Ile Lys Gly Val Ile Val His
1               5                   10

Lys Ile Glu Gly Ile Leu Phe Gly Gly Cys Gly Glu
            15                  20

Thr Tyr Gln Ser Arg Val Thr His Pro His Leu Pro
25                  30                  35

Arg Ala Leu Met Arg Ser Thr Thr Lys Cys
            40                  45

(2) INFORMATION FOR SEQ ID NO:97:
```

(i) SEQUENCE CHARACTERISTICS:
            (A) LENGTH: 46 amino acids
            (B) TYPE: amino acid
            (D) TOPOLOGY: linear (ii) MOLECULE TYPE: peptide (xi) SEQUENCE DESCRIPTION: SEQ ID NO:97:

Ile Ser Ile Thr Glu Ile Arg Thr Val Ile Val Thr
 1               5                  10

Arg Ile Glu Thr Ile Leu Phe Gly Gly Cys Gly Glu
            15                  20

Thr Tyr Gln Ser Arg Val Thr His Pro His Leu Pro
25                  30                  35

Arg Ala Leu Met Arg Ser Thr Thr Lys Cys
                40                  45

(2) INFORMATION FOR SEQ ID NO:98:

(i) SEQUENCE CHARACTERISTICS:
            (A) LENGTH: 42 amino acids
            (B) TYPE: amino acid
            (D) TOPOLOGY: linear (ii) MOLECULE TYPE: peptide (xi) SEQUENCE DESCRIPTION: SEQ ID NO:98:

Ile Ser Glu Ile Lys Gly Val Ile Val His Lys Ile
 1               5                  10

Glu Gly Ile Gly Gly Cys Gly Glu Thr Tyr Gln Ser
            15                  20

Arg Val Thr His Pro His Leu Pro Arg Ala Leu Met
25                  30                  35

Arg Ser Thr Thr Lys Cys
                40

(2) INFORMATION FOR SEQ ID NO:99:

(i) SEQUENCE CHARACTERISTICS:
            (A) LENGTH: 42 amino acids
            (B) TYPE: amino acid
            (D) TOPOLOGY: linear (ii) MOLECULE TYPE: peptide (xi) SEQUENCE DESCRIPTION: SEQ ID NO:99:

Met Thr Glu Ile Arg Thr Val Ile Val Thr Arg Met
 1               5                  10

Glu Thr Met Gly Gly Cys Gly Glu Thr Tyr Gln Ser
            15                  20

Arg Val Thr His Pro His Leu Pro Arg Ala Leu Met
25                  30                  35

Arg Ser Thr Thr Lys Cys
                40

(2) INFORMATION FOR SEQ ID NO:100:

(i) SEQUENCE CHARACTERISTICS:
            (A) LENGTH: 42 amino acids
            (B) TYPE: amino acid
            (D) TOPOLOGY: linear (ii) MOLECULE TYPE: peptide (xi) SEQUENCE DESCRIPTION: SEQ ID NO:100:

Leu Ser Glu Ile Lys Gly Val Ile Val His Lys Leu
1               5                   10

Glu Gly Val Gly Gly Cys Gly Glu Thr Tyr Gln Ser
            15                  20

Arg Val Thr His Pro His Leu Pro Arg Ala Leu Met
25                  30                  35

Arg Ser Thr Thr Lys Cys
        40

(2) INFORMATION FOR SEQ ID NO:101:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO:101:

Lys Lys Lys Ile Ile Thr Ile Thr Arg Ile Ile Thr
1               5                   10

Ile Ile Thr Thr Ile Asp Gly Gly Cys Gly Glu Thr
            15                  20

Tyr Gln Ser Arg Val Thr His Pro His Leu Pro Arg
25                  30                  35

Ala Leu Met Arg Ser Thr Thr Lys Cys
            40                  45

(2) INFORMATION FOR SEQ ID NO:102:

(i) SEQUENCE CHARACTERISTICS:
        (A) LENGTH: 63 amino acids
        (B) TYPE: amino acid
        (D) TOPOLOGY: linear (ii) MOLECULE TYPE: peptide (xi) SEQUENCE DESCRIPTION: SEQ ID NO:102:

Thr Ala Lys Ser Lys Lys Phe Pro Ser Tyr Thr Ala
1               5                   10

Thr Tyr Gln Phe Gly Gly Lys Lys Lys Ile Ile Thr
            15                  20

Ile Thr Arg Ile Ile Thr Ile Ile Thr Thr Ile Asp
25                  30                  35

Gly Gly Cys Gly Glu Thr Tyr Gln Ser Arg Val Thr
            40                  45

His Pro His Leu Pro Arg Ala Leu Met Arg Ser Thr
    50                  55                  60

Thr Lys Cys (2) INFORMATION FOR SEQ ID NO:103:

(i) SEQUENCE CHARACTERISTICS:
        (A) LENGTH: 56 amino acids
        (B) TYPE: amino acid
        (D) TOPOLOGY: linear (ii) MOLECULE TYPE: peptide (xi) SEQUENCE DESCRIPTION: SEQ ID NO:103:

-continued

```
Lys Lys Lys Ile Ile Thr Ile Thr Arg Ile Ile Thr
1               5                   10

Ile Ile Thr Thr Ile Asp Gly Gly Cys Lys Tyr Gly
            15                  20

Glu Asn Ala Val Thr Asn Val Arg Gly Asp Leu Gln
25                  30                  35

Val Leu Ala Gln Lys Ala Ala Arg Cys Leu Pro Thr
            40                  45

Ser Phe Asn Tyr Gly Ala Ile Lys
50                  55
```

(2) INFORMATION FOR SEQ ID NO:104:

(i) SEQUENCE CHARACTERISTICS:
        (A) LENGTH: 72 amino acids
        (B) TYPE: amino acid
        (D) TOPOLOGY: linear (ii) MOLECULE TYPE: peptide (xi) SEQUENCE DESCRIPTION: SEQ ID NO:104:

```
Thr Ala Lys Ser Lys Lys Phe Pro Ser Tyr Thr Ala
1               5                   10

Thr Tyr Gln Phe Gly Gly Lys Lys Lys Ile Ile Thr
            15                  20

Ile Thr Arg Ile Ile Thr Ile Ile Thr Thr Ile Asp
25                  30                  35

Gly Gly Cys Thr Tyr Gly Thr Gln Pro Ser Arg Arg
            40                  45

Gly Asp Met Ala Ala Leu Ala Gln Arg Leu Ser Arg
50                  55                  60

Cys Leu Pro Thr Ser Phe Asn Tyr Gly Ala Val Lys
            65                  70
```

(2) INFORMATION FOR SEQ ID NO:105:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:105:

```
Ile Ser Met Thr Glu Met Arg Thr Val Ile Val Thr
1               5                   10

Arg Met Glu Thr Val Leu Phe
            15
```

(2) INFORMATION FOR SEQ ID NO:106:

(i) SEQUENCE CHARACTERISTICS:
        (A) LENGTH: 31 amino acids
        (B) TYPE: amino acid
        (D) TOPOLOGY: linear (ii) MOLECULE TYPE: peptide (xi) SEQUENCE DESCRIPTION: SEQ ID NO:106:

```
Ile Ser Met Thr Glu Met Arg Thr Val Ile Val Thr
1               5                   10
```

-continued

```
Arg Met Glu Thr Val Leu Phe Gly Gly Glu His Trp
        15                  20

Ser Tyr Gly Leu Arg Pro Gly
25                  30
```